(12) United States Patent
Hibino et al.

(10) Patent No.: US 7,094,914 B2
(45) Date of Patent: Aug. 22, 2006

(54) PROCESS FOR PRODUCING CHROMONE COMPOUND

(75) Inventors: Hiroaki Hibino, Toyonaka (JP); Susumu Ohtsuka, Ibaraki (JP); Yasunobu Miyamoto, Toyonaka (JP); Tomoyasu Yoshida, Oita (JP); Itsuo Okumoto, Sakai-gun (JP)

(73) Assignees: Sumitomo Chemical Company, Limited, Osaka (JP); Ono Pharmaceutical Co., Ltd., Osaka (JP)

( * ) Notice: Subject to any disclaimer, the term of this patent is extended or adjusted under 35 U.S.C. 154(b) by 145 days.

(21) Appl. No.: 10/506,119

(22) PCT Filed: Feb. 27, 2003

(86) PCT No.: PCT/JP03/02182

§ 371 (c)(1),
(2), (4) Date: Aug. 27, 2004

(87) PCT Pub. No.: WO03/080555

PCT Pub. Date: Oct. 2, 2003

(65) Prior Publication Data

US 2005/0085664 A1    Apr. 21, 2005

(30) Foreign Application Priority Data

Feb. 28, 2002   (JP) ............... 2002-053315
Feb. 28, 2002   (JP) ............... 2002-053316
Jun. 11, 2002   (JP) ............... 2002-169675
Jun. 11, 2002   (JP) ............... 2002-169676

(51) Int. Cl.
C07D 311/24    (2006.01)
C07C 205/37    (2006.01)

(52) U.S. Cl. ..................... 549/402; 549/401
(58) Field of Classification Search ............... 549/401, 549/402
See application file for complete search history.

(56) References Cited

U.S. PATENT DOCUMENTS

| 3,465,037 A | 9/1969 | Jenkner |
| 3,738,823 A | 6/1973 | Gier et al. |
| 4,780,469 A | 10/1988 | Toda et al. |
| 4,847,275 A | 7/1989 | Toda et al. |
| 4,939,141 A | 7/1990 | Toda et al. |
| 5,446,058 A | 8/1995 | Toda et al. |
| 5,459,134 A | 10/1995 | Toda et al. |

FOREIGN PATENT DOCUMENTS

EP    309711    4/1989

(Continued)

OTHER PUBLICATIONS

Terry et al, JACS, vol. 47, p. 1067-1078 (1925).*

(Continued)

*Primary Examiner*—Bernard Dentz
(74) *Attorney, Agent, or Firm*—Wenderoth, Lind & Ponack, L.L.P.

(57) ABSTRACT

A process for producing a dicarboxylic acid compound represented by the formula (4):

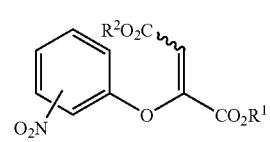

(4)

wherein $R^1$ and $R^2$ are the same or different and each represents lower alkyl and the wavy line indicates that this compound is the E- or Z-isomer or a mixture of them, characterized by reacting a compound represented by the formula (2):

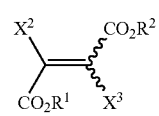

(2)

wherein $R^1$, $R^2$ and the wavy line have the same meanings as the above, and one of $X^2$ and $X^3$ represents hydrogen and the other represents halogen, with nitrophenol represented by the formula (3):

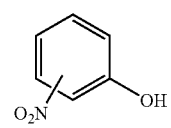

(3)

in the presence of a base; a process for producing a nitrochromone compound represented by the formula (5):

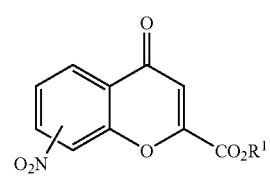

(5)

wherein $R^1$ has the same meaning as the above, characterized by reacting the dicarboxylic acid compound or carboxylic acid thereof with an acid; a process for producing an aminochromone compound which comprises reducing the nitrochromone compound; and a process for producing an amidochromone compound which comprises acylating the aminochromone compound are provided.

6 Claims, No Drawings

FOREIGN PATENT DOCUMENTS

| | | |
|---|---|---|
| EP | 485984 | 5/1992 |
| EP | 634409 | 1/1995 |
| GB | 1292602 | 10/1972 |
| GB | 1585168 | 2/1981 |
| JP | 56-90017 | 7/1981 |
| JP | 56-90018 | 7/1981 |
| JP | 61-050977 | 3/1986 |
| JP | 3-95144 | 4/1991 |

OTHER PUBLICATIONS

Roberts and Caserio, Basic Principles of Organic Chemistry, W. A. Benjamin, Inc., New York, New York, p. 576-581 (1965).*

Martin J. Stoermer, et al., "A selective and versatile synthesis of substituted chromones via addition of phenols to dimethyl acetylenedicarboxylate", Australian Journal of Chemistry, vol. 48, No. 3, pp. 677-686, 1995.

Miroslav Protiva et al., "Potential cerebral stimulants: esters of 2-(dimethylamino)ethanol with some lipophilic carboxylic acids", Collection of Czechoslovak Chemical Communications, vol. 55, No. 5, pp. 1278-1289, 1990.

G. Barker et al., "Benzopyrones. Part 1. 6-Amino- and 6-Hydroxy-2-substituted Chromones", J. Chem. Soc. (C), pp. 2230-2233, 1970.

R. Griera et al., "Synthesis and pharmacological evaluation of new cysLT$_1$ receptor antagonists", Eur. J. Med. Chem., 32, pp. 547-570, 1997.

M.J. Rosen et al., "Reactions of Adsorbed Organic Molecules. I. Bromination of Diethyl Fumarate on a Silica Surface", J. Physical Chemistry, vol. 74, No. 11, pp. 2303-2309, 1970.

Bull. Soc. Chim. Belg., "Une Nouvelle Methode de Bromation Le Tribromure de Tetrabutylammonium", vol. 93, No. 2, pp. 157-158, 1984.

Hisao Nakai, et al., "New Potent Antagonists of Leukotrienes c$_4$ and D$_4$. 1. Synthesis and Structure-Activity Relationships", J. Med. Chem., pp. 84-91, 1988.

B. Vernon Cheney et al., "Structure -Activity Correlations for a Series of Antiallergy Agents. Oxanilic, Quinaldic, and Benzopyran-2-carboxylic Acids", Journal of Medicinal Chemistry, vol. 21, No. 9, pp. 936-940, 1978.

G.P. Ellis et al., "Benzpyrones. 14. Synthesis and Antiallergic Properties of Some N-Tetrazolylcarboxamides and Related Compounds", Journal of Medicinal Chemistry, vol. 21, No. 11, pp. 1120-1126, 1978.

César Raposo et al., "Chromenone Derivatives as Receptors for N-Benzoylamino Acids", J. Chem. Soc., 1, pp. 2113-2116, 1994.

César Raposo et al., "Malonic Acid Receptors With Decarboxylative Activity", Tetrahedron, vol. 52, No. 37, pp. 12323-12332, 1996.

Richard J. Strunk et al., "Free-Radical Reduction and Dehalogenation of Vicinal Dihalides by Tri-n-butyltin Hydride", Journal of the American Chemical Society, 92(9), pp. 2849-2856, CODEN: JACSAT; ISSN: 0002-7863, XP002370951, 1970.

G. Barker et al., "Benzopyrones. 9. Synthesis and pharmacology of some novel bischromones", Journal of Medicinal Chemistry, 16(1), pp. 87-89, CODEN: JMCMAR; ISSN: 0022-2623, XP002370952, 1973.

Alan O. Fitton et al, "Pharmacologically Active 4-Oxo-4H-chromen-2-carboxylic Acids. Part II. The Synthesis of 4-Oxo-4H-chromen-2-carboxylic Acids containing a Fused Imidazole or Oxazole Ring", Journal of the Chemical Society [Section] C: Organic, (18), pp. 2518-2522, CODEN: JSOOAX; ISSN: 0022-4952, XP008060742, 1970.

Geneviéve Mouysset al. al., "Synthése et activité anti-allergique de quelques alcools benzopyroniques et apparentés", European Journal of Medicinal Chemistry, 23(2), pp. 199-202, CODEN: EJMCA5; ISSN: 0223-5234, XP002370954, 1988.

V.A. Zagorevskii et al., "Synthesis of Substituted Chromone-2-Carboxylic Acids and Their Esters", Journal of General Chemistry USSR., vol. 30, pp. 3850-3853, XP008060744, 1960, Usconsultants Bureau, New York, NY, ISSN: 0044-457X.

G.P. Ellis et al., "Benzpyrones. 7. Synthesis and Antiallergic Activity of Some 2-(5-Tetrazolyl)chromones", Journal of Medicinal Chemistry, 15(8), pp. 865-867, CODEN: JMCMAR; ISSN: 0022-2623, XP002370955, 1972.

* cited by examiner

PROCESS FOR PRODUCING CHROMONE COMPOUND

This application is a national stage entry of PCT/JP03/02182 filed Feb. 27, 2003.

TECHNICAL FIELD

The present invention relates to a process for producing a chromone compound, which is a useful compound as a pharmaceutical intermediate.

BACKGROUND ART

An aminochromone compound is a useful compound as a pharmaceutical intermediate (e.g. Eur. J. Med. Chem., 32, 547(1997), JP-A 3-95144, etc.) and a known process for producing said compound comprises reacting a nitrochromone compound with hydrogen in the presence of a palladium catalyst (e.g. J. Chem. Soc. (C), 2230(1970), etc.). However, such a process is unsatisfactory as an industrial production process because it has a tendency to produce over-reduced compounds, wherein the carbon-carbon double bond at the 2-position and/or the carbonyl group at the 4-position of a nitrochromone compound are also reduced in addition to the nitro group, as byproducts and therefore the yield of the aminochromone compound thus obtained is low.

Another known process of synthesizing a compound having a chromone skeleton comprises hydrolyzing a dicarboxylic acid compound obtained by addition reaction of an expensive acetylene compound and a phenol compound to obtain carboxylic acid and then cyclizing said carboxylic acid to obtain a chromone compound (Aust. J. Chem., 48, 677(1995)). However, said process is not necessarily satisfactory industrially because it requires an expensive acetylene compound. Further, as a process for producing a nitrochromone compound, a process involving a use of nitro-substituted 2-hydroxyacetophenone as a starting material (JP-A 3-95144) is known and the nitro-substituted 2-hydoxyacetophenone is produced by nitration of 2-hydroxyacetophenone. However, position-selectivity for the nitro group-introduction in the nitration is low and as a result, isomers with nitro groups at different substitution positions are produced as byproducts. Therefore, a step of removing the isomers is required and thus said process involving a use of nitro-substituted 2-hydroxyacetophenon as a starting material is not necessarily an industrially satisfactory process.

DISCLOSURE OF INVENTION

According to a process of the present invention, a dicarboxylic acid compound represented by the following formula (4) can be produced advantageously by using a dihalosuccinic acid compound obtained from a fumaric acid or maleic acid compound, which is easily available, and a compound derived from said dihalosuccinic acid compound, and then a nitrochromone compound can be easily obtained from said dicarboxylic acid.

An aminochromone compound can be produced by selective reduction of the nitrochromone compound thus obtained and consequently, an amidochromone compound useful as a pharmaceutical intermediate can be industrially advantageously produced from said aminochromone compound.

That is, the present invention provides
1. a process for producing a dicarboxylic acid compound represented by the formula (4):

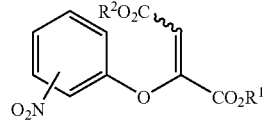

(4)

wherein $R^1$ and $R^2$ and the wavy line are as defined below; which comprises reacting at least one compound selected from the group consisting of dihalosuccinic acid compound represented by the formula (1):

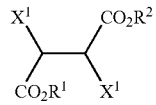

(1)

wherein $R^1$ and $R^2$ are the same or different and independently represent a lower alkyl group and $X^1$ represents a halogen atom, and a compound represented by the formula (2):

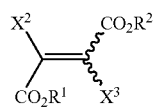

(2)

wherein $R^1$ and $R^2$ are as defined above, one of $X^2$ and $X^3$ represents a hydrogen atom and the other represents a halogen atom, and the wavy line indicates that this compound is the E- or Z-isomer or a mixture of them, with a nitrophenol compound represented by the formula (3):

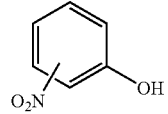

(3)

in the presence of a base;
2. a dicarboxylic acid compound represented by the formula (4a):

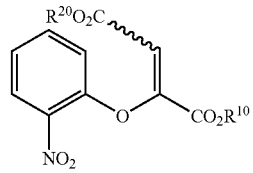

(4a)

wherein $R^{10}$ and $R^{20}$ independently represent a hydrogen atom or a lower alkyl group and the wavy line is as defined above;

3. a process for producing a threo-dihalosuccinic acid compound, which comprises adding a maleic acid compound to a halogenating agent;
4. a process for producing a nitrochromone compound represented by the formula (5):

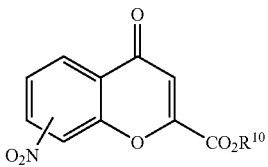

(5)

wherein $R^{10}$ is as defined below; which comprises reacting a dicarboxylic acid compound represented by formula (4'):

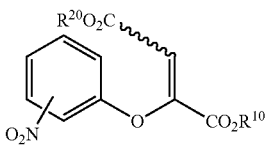

(4')

wherein $R^{10}$ and $R^{20}$ are the same or different and independently represent a hydrogen atom or a lower alkyl group, with an acid; and
5. a process for producing an aminochromone compound represented by the formula (6):

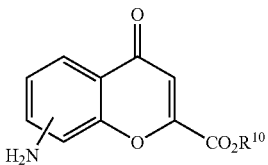

(6)

wherein $R^{10}$ is as defined above; which comprises reacting the nitrochromone compound represented by the formula (5) with hydrogen in the presence of a metal catalyst and a base in an organic solvent.

MODE FOR CARRYING OUT THE INVENTION

With respect to the compounds represented by the above formulas (1) to (6), (4a) and (4') and the compounds represented by the following formulas (7), (8) and (9), the lower alkyl group denoted by $R^1$, $R^2$, $R^{10}$ or $R^{20}$ includes $C_{1-6}$ straight chain or branched chain alkyl groups and specific examples thereof are methyl, ethyl, propyl, butyl, pentyl, hexyl, and the like.

The halogen atom denoted by $X^1$ includes chlorine, bromine and iodine. When $X^2$ or $X^3$ represents a halogen atom, said halogen atom includes the above-mentioned halogen atoms.

First, a process for producing a dicarboxylic acid compound represented by the formula (4) which comprises reacting at least one compound selected from the group consisting of a dihalosuccinic acid compound represented by the formula (1) and a compound represented by the formula (2) with a nitrophenol compound represented by the formula (3) in the presence of a base will be explained.

The dihalosuccinic acid compound represented by the formula (1) includes, for example, dimethyl 2,3-dichlorosuccinate, dimethyl 2,3-dibromosuccinate, dimethyl 2,3-diiodosuccinate, diethyl 2,3-dichlorosuccinate, diethyl 2,3-dibromosuccinate, diethyl 2,3-diiodosuccinate, di(n-propyl) 2,3-dichlorosuccinate, di(n-propyl) 2,3-dibromosuccinate, di(n-propyl) 2,3-diiodosuccinate, diisopropyl 2,3-dichlorosuccinate, diisopropyl 2,3-dibromosuccinate, diisopropyl 2,3-diiodosuccinate, di(n-butyl) 2,3-dichlorosuccinate, di(n-butyl) 2,3-dibromosuccinate, di(n-butyl) 2,3-diiodosuccinate, diisobutyl 2,3-dichlorosuccinate, diisobutyl 2,3-dibromosuccinate, diisobutyl 2,3-diiodosuccinate, di(sec-butyl) 2,3-dichlorosuccinate, di(sec-butyl) 2,3-dibromosuccinate, di(sec-butyl) 2,3-diiodosuccinate, di(tert-butyl) 2,3-dichlorosuccinate, di(tert-butyl) 2,3-dibromosuccinate, di(tert-butyl) 2,3-diiodosuccinate, di(n-pentyl) 2,3-dichlorosuccinate, di(n-pentyl) 2,3-dibromosuccinate, di(n-pentyl) 2,3-diiodosuccinate, di(n-hexyl) 2,3-dichlorosuccinate, di(n-hexyl) 2,3-dibromosuccinate and di(n-hexyl) 2,3-diiodosuccinate.

With respect to the dihalosuccinic acid compound represented by the formula (1), there are two isomers: erythro-isomer and threo-isomer. The dihalosuccinic acid compound represented by the formula (1) may be in the erythro-form or the threo-form or a composition containing both of them. For the present reaction, either the erythro-isomer or the threo-isomer may be used, or a composition containing the erythro-isomer and the threo-isomer in an optional ratio may be used. The dihalosuccinic acid compound represented by the formula (1) may be commercially available or may be prepared, for example, according to a method described in JP-A 56-90017, by reacting a fumaric acid or maleic acid compound represented by the formula (7):

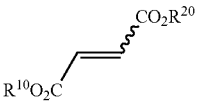

(7)

wherein $R^{10}$, $R^{20}$ and the wavy line are as defined above, with a halogenating agent in the presence of halogenated hydracid.

When at least one of $R^{10}$ and $R^{20}$ represents a hydrogen atom, a dihalosuccinic acid or its half-esterified compound obtained by the above-mentioned halogenation can be appropriately esterified to obtain the dihalosuccinic acid compound represented by the formula (1). A method of the esterification is not particularly limited as long as it is a method of synthesizing ester from carboxylic acid. Known esterification methods that may be employed are described, for example, in Jikken Kagaku Koza vol. 22, 4th Ed., the Chemical Society of Japan, p. 43, Shin Jikken Kagaku Koza 14, the Chemical Society of Japan, p. 1002, and Comprehensive Organic Functional Group Transformations, PERGAMON(1995) vol. 5, p. 121.

For example, the dihalosuccinic acid compound represented by the formula (1) can be derived by a similar method to the following esterification of threo-dihalosuccinic acid, for example, by reaction with an alcohol compound represented by the formula $R^1OH$ or $R^2OH$ in the presence of an acid catalyst.

Specific examples of the fumaric acid compound or the maleic acid compound include, for example, fumaric acid, maleic acid, monomethyl fumarate, monomethyl maleate, dimethyl fumarate, dimethyl maleate, diethyl fumarate, diethyl maleate, di(n-propyl) fumarate, di(n-propyl) maleate, diisopropyl fumarate, diisopropyl maleate, di(n-butyl) fumarate, di(n-butyl) maleate, diisobutyl fumarate, diisobutyl maleate, di(sec-butyl) fumarate, di(sec-butyl) maleate, di(tert-butyl) fumarate, di(tert-butyl) maleate, di(n-pentyl) fumarate, di(n-pentyl) maleate, di(n-hexyl) fumarate, and di(n-hexyl) maleate.

The dihalosuccinic acid compound represented by the formula (1) may be preferably a composition in which the proportion of a threo-dihalosuccinic acid compound is higher than that of an erythro-dihalosuccinic acid compound, specifically a composition in which the proportion of a threo-dihalosuccinic acid compound is 70% or higher, more preferably a composition in which the proportion of a threo-dihalosuccinic acid compound is 85% or higher. Such a composition can be obtained, for example, by adding a maleic acid compound to a halogenating agent.

Specific examples of the maleic acid compound are maleic acid compounds represented by the formula (8):

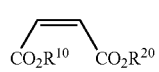

(8)

wherein $R^{10}$ and $R^{20}$ are the same or different and independently represent a hydrogen atom or an alkyl group.

The halogenating agent includes, for example, halogen such as chlorine or bromine, and halogen addition compounds such as a tetramethylammonium bromide-bromine addition compound, a dioxane-bromine addition compound, a pyridine hydrobromide-dibromide addition compound or a dibenzo-18-crown-6 bromine complex and among them bromine is preferred. The halogenating agent may be used as it is or as a solution after dissolving in an organic solvent inert to the reaction.

The organic solvent inert to the reaction includes, for example, halogenated hydrocarbon solvents such as dichloromethane, dichloroethane, chloroform, carbon tetrachloride, chlorobenzene or dichlorobenzene.

The amount used of the halogenating agent is usually 1 mole or more per 1 mole of the maleic acid compound and there is no upper limit. However, if the amount used is too much, the unreacted halogenating agent increases, which results in economical disadvantage. Therefore, the amount used of the halogenating agent is practically 2 moles or less, preferably 1.5 moles or less per 1 mole of the maleic acid compound.

If the reaction temperature is too low, the reaction is difficult to progress and if it is too high, the halogenating agent is easy to lose. Therefore, the reaction temperature is usually 0 to 80° C., preferably 20 to 60° C.

The reaction may be carried out in an organic solvent inert to the reaction. The organic solvent inert to the reaction includes, for example, halogenated hydrocarbon solvents such as dichloromethane, dichloroethane, chloroform, carbon tetrachloride, chlorobenzene or dichlorobenzene and the amount used thereof is not particularly limited.

By such a reaction, the proportion of a threo-dihalosuccinic acid compound in the resulting dihalosuccinic acid compound can be increased and the threo-dihalosuccinic acid compound can be produced selectively and in high yield. Particularly, when a maleic acid compound represented by the formula (8) is used as the maleic acid compound, a dihalosuccinic acid compound that contains a threo-dihalosuccinic acid compound having a relative configuration represented by the formula (9):

(9)

wherein $R^{10}$, $R^{20}$ and $X^1$ are as defined above, in a proportion of 85% or more can be obtained easily.

For the reaction of the halogenating agent and the maleic acid compound, a reaction container may be previously charged with the entire amount of the halogenating agent to be used and the maleic acid compound may be then added thereto, or a reaction container may be charged with a portion of the halogenating agent to be used and the remaining halogenating agent and the maleic acid compound may be then added in parallel thereto. Although the maleic acid compound may be added at once to the halogenating agent, it is preferably added continuously or intermittently.

After completion of the reaction, the reaction solution is usually mixed with a reducing agent such as sodium sulfite, sodium hydrogen sulfite or sodium thiosulfate to remove the unreacted halogenating agent. Then, the reaction solution can be separated by addition of water and, if necessary, a water-insoluble organic solvent to obtain an organic layer containing a threo-dihalosuccinic acid compound. The organic solvent can be distilled out of the organic layer to isolate the threo-dihalosuccinic acid compound. The isolated threo-dihalosuccinic acid compound may be further purified by a conventional purification means such as column chromatography, recrystallization or distillation.

The reducing agent may be used as it is or in the form of an aqueous solution. When an aqueous solution of the reducing agent is used, water need not be added in a step of separating a reaction solution.

The water-insoluble organic solvent includes, for example, halogenated hydrocarbon solvents such as dichloromethane, dichloroethane, chloroform, carbon tetrachloride, chlorobenzene or dichlorobenzene; aromatic hydrocarbon solvents such as toluene or xylene; and aliphatic hydrocarbon solvents such as hexane or heptane and the amount used thereof is not particularly limited.

Specific examples of the threo-dihalosuccinic acid compound are threo-2,3-dichlorosuccinic acid, threo-2,3-dibromosuccinic acid, dimethyl threo-2,3-dichlorosuccinate, dimethyl threo-2,3-dibromosuccinate, diethyl threo-2,3-dichlorosuccinate, diethyl threo-2,3-dibromosuccinate, di(n-propyl) threo-2,3-dichlorosuccinate, di(n-propyl) threo-2,3-dibromosuccinate, diisopropyl threo-2,3-dichlorosuccinate, diisopropyl threo-2,3-dibromosuccinate, di(n-butyl) threo-2,3-dichlorosuccinate, di(n-butyl) threo-2,3-dibromosuccinate, diisobutyl threo-2,3-dichlorosuccinate, diisobutyl threo-2,3-dibromosuccinate, di(sec-butyl) threo-2,3-dichlorosuccinate, di(sec-butyl) threo-2,3-dibromosuccinate, di(tert-butyl) threo-2,3-dichlorosuccinate, di(tert-butyl) threo-2,3-dibromosuccinate, di(n-pentyl) threo-2,3-dichlorosuccinate, di(n-pentyl) threo-2,3-dibromosuccinate, di(n-hexyl) threo-2,3-dichlorosuccinate, and di(n-hexyl) threo-2,3-dibromosuccinate.

When $R^{10}$ and $R^{20}$ in the formula (8) independently represent a lower alkyl group, the resulting product containing the threo-dihalosuccinic acid compound represented by the formula (9) can be used as the dihalosuccinic acid compound for reaction with the nitrophenol compound represented by the formula (3).

When at least one of $R^{10}$ and $R^{20}$ in the formula (8) represents a hydrogen atom, the resulting product containing dihalosuccinic acid and its half ester compound which are the threo-dihalosuccinic acid compound represented by the formula (9) (wherein at least one of $R^{10}$ and $R^{20}$ represents a hydrogen atom) can be easily converted into a dihalosuccinic acid compound containing the threo-dihalosuccinic acid compound represented by the formula (9) (wherein, $R^{10}$ and $R^{20}$ independently represent a lower alkyl group) by a known esterification method, similarly to esterification of the dihalosuccinic acid compound obtained by halogenation of the compound represented by the formula (7). For example, such a esterification method can be performed by using a suitable lower alkyl alcohol such as $R^{10}OH$ or $R^{20}OH$ in the presence of an acid catalyst or by reacting a reactive derivative of the threo-dihalosuccinic acid, such as a threo-dihalosuccinic acid halide, derived from the carboxylic acid and a carboxylic acid activator such as thionyl chloride with the above-mentioned lower alkyl alcohol, in the presence of a catalyst such as a base if necessary.

The compound (2) can be obtained by, for example, reacting the above-mentioned compound (1) with a base. The base includes, for example, organic bases such as triethylamine and inorganic bases such as sodium carbonate or sodium hydrogen carbonate, and the amount used thereof is usually 1 to 2 moles per 1 mole of the dihalosuccinic acid compound (1).

Depending on reaction conditions, a portion of the dihalosuccinic acid compound (1) may remain unreacted and a mixture of the dihalosuccinic acid compound (1) and the compound (2) may be obtained, which mixture may be also used for the reaction with the nitrophenol represented by the formula (3).

The compound (2) includes, for example, dimethyl 2-chlorofumarate, dimethyl 2-chloromaleate, dimethyl 2-bromofumarate, dimethyl 2-bromomaleate, dimethyl 2-iodofumarate, dimethyl 2-iodomaleate, diethyl 2-chlorofumarate, diethyl 2-chloromaleate, diethyl 2-bromofumarate, diethyl 2-bromomaleate, diethyl 2-iodofumarate, diethyl 2-iodomaleate, di(n-propyl) 2-chlorofumarate, di(n-propyl) 2-chloromaleate, di(n-propyl) 2-bromofumarate, di(n-propyl) 2-bromomaleate, di(n-propyl) 2-iodofumarate, di(n-propyl) 2-iodomaleate, diisopropyl 2-chlorofumarate, diisopropyl 2-chloromaleate, diisopropyl 2-bromofumarate, diisopropyl 2-bromomaleate, diisopropyl 2-iodofumarate, diisopropyl 2-iodomaleate, di(n-butyl) 2-chlorofumarate, di(n-butyl) 2-chloromaleate, di(n-butyl) 2-bromofumarate, di(n-butyl) 2-bromomaleate, di(n-butyl) 2-iodofumarate, di(n-butyl) 2-iodomaleate, diisobutyl 2-chlorofumarate, diisobutyl 2-chloromaleate, diisobutyl 2-bromofumarate, diisobutyl 2-bromomaleate, diisobutyl 2-iodofumarate, diisobutyl 2-iodomaleate, di(sec-butyl) 2-chlorofumarate, di(sec-butyl) 2-chloromaleate, di(sec-butyl) 2-bromofumarate, di(sec-butyl) 2-bromomaleate, di(sec-butyl) 2-iodofumarate, di(sec-butyl) 2-iodomaleate, di(sec-butyl) 2-chlorofumarate, di(sec-butyl) 2-chloromaleate, di(sec-butyl) 2-bromofumarate, di(sec-butyl) 2-bromomaleate, di(sec-butyl) 2-iodofumarate, di(sec-butyl) 2-iodomaleate, di(tert-butyl) 2-chlorofumarate, di(tert-butyl) 2-chloromaleate, di(tert-butyl) 2-bromofumarate, di(tert-butyl) 2-bromomaleate, di(tert-butyl) 2-iodofumarate, di(tert-butyl) 2-iodomaleate, di(n-pentyl) 2-chlorofumarate, di(n-pentyl) 2-chloromaleate, di(n-pentyl) 2-bromofumarate, di(n-pentyl) 2-bromomaleate, di(n-pentyl) 2-iodofumarate, di(n-pentyl) 2-iodomaleate, di(n-hexyl) 2-chlorofumarate, di(n-hexyl) 2-chloromaleate, di(n-hexyl) 2-bromofumarate, di(n-hexyl) 2-bromomaleate, di(n-hexyl) 2-iodofumarate, and di(n-hexyl) 2-iodomaleate. Preferably the Z-forms (fumaric acid type) are used.

The nitrophenol compound represented by the formula (3) (hereinafter, referred as the nitrophenol compound (3)) includes, for example, 2-nitrophenol, 3-nitrophenol and 4-nitrophenol.

The dicarboxylic compound (4) may be produced by reacting either the dihalosuccinic acid compound (1) or the compound (2) with the nitrophenol (3) or by reacting a mixture of the dihalosuccinic acid compound (1) and the compound (2) with the nitrophenol (3).

Either one of the nitrophenol compound (3) and at least one compound selected from the group consisting of the dihalosuccinic acid compound (1) and the compound (2) may be used in an amount of 1 mole or more per 1 mole of the other.

The reaction of at least one compound selected from the group consisting of the dihalosuccinic acid compound (1) and the compound (2) with the nitrophenol compound (3) is usually carried out in an organic solvent. The organic solvent includes, for example, aprotic polar solvents such as N,N-dimethylformamide, N-methylpyrrolidone, 1, 3-dimethyl-2-imidazolidinone, dimethyl sulfoxide, sulfolane, acetonitrile or propionitrile; alcohol solvents such as methanol or ethanol; ketone solvents such as acetone or methyl isobutyl ketone; aromatic hydrocarbon solvents such as toluene or xylene; halogenated hydrocarbon solvents such as dichloromethane, dichloroethane, chlorobenzene or dichlorobenzene; ether solvents such as dimethyl ether, methyl tert-butyl ether or tetrahydrofuran; ester solvents such as ethyl acetate; and pyridine solvents such as pyridine or 5-ethyl-2-methylpyridine. These solvents may be used alone or as a mixture of two or more of these. Preferred are single solvents or mixtures of aprotic polar solvents, aromatic hydrocarbon solvents and halogenated hydrocarbon solvents. The amount used of the solvent is usually 2 to 50 parts by weight per 1 part by weight of the nitrophenol compound (3).

The base includes, for example, alkali metal hydrides such as sodium hydride or potassium hydride; alkaline earth metal hydrides such as calcium hydride; alkali metal hydroxides such as lithium hydroxide, sodium hydroxide or potassium hydroxide; alkaline earth metal hydroxides such as calcium hydroxide or barium hydroxide; alkali metal carbonates such as lithium carbonate, sodium carbonate or potassium carbonate; alkaline earth metal carbonates such as calcium carbonate; alkali metal hydrogen carbonates such as sodium hydrogen carbonate or potassium hydrogen carbonate; and organic amines such as triethylamine or pyridine. These bases may be used alone or as a mixture of two or more of these. Preferred are alkali metal hydrides and alkali metal carbonates and more preferred are alkali metal carbonates.

The amount used of the base may be suitably set based on the amounts used of the nitrophenol (3) and at least one compound selected from the group consisting of the dihalosuccinic acid compound (1) and the compound (2). For example, when the dihalosuccinic acid compound (1) and the nitrophenol compound (3) are reacted and the amount used of the nitrophenol compound (3) is smaller than that of the other, the amount used of the base is usually 2 moles or more per 1 mole of the nitrophenol compound (3) and when the amount used of the dihalosuccinic acid compound (1) is smaller than that of the other, the amount used of the base is usually 2 moles or more per 1 mole of the dihalosuccinic acid compound (1). Further, for example, when the compound (2) and the nitrophenol (3) are reacted and the amount used of the nitrophenol compound (3) is smaller than that of the other, the amount used of the base is usually 1 mole or more per 1 mole of the nitrophenol compound (3) and when the amount used of the compound (2) is smaller than that of the other, the amount used of the base is usually 1 mole or more per 1 mole of compound (2). There is no upper limit of the amount used of the base. However, if the amount used of the base is too much, it will result in economical disadvantage and therefore, the amount used of the base is practically 10 moles or less, preferably 5 moles or less per 1 mol of either one of the nitrophenol compound (3) and at least one compound selected from the group consisting of the dihalosuccinic acid compound (1) and the compound (2), wherein the one is used in a smaller amount than the amount used of the other.

The reaction temperature is usually 20 to 150° C. Further, the reaction may be usually carried out by mixing and contacting at least one compound selected from the group consisting of the dihalosuccinic acid compound (1) and the compound (2), the nitrophenol compound (3) and the base in an organic solvent. The order of mixing them is not particularly limited and however, it is preferable to mix at least one compound selected from the group consisting of the dihalosuccinic acid compound (1) and the compound (2) with a mixture of the nitrophenol compound (3) and the base.

Coexistence of a phase transfer catalyst in the reaction system makes it possible to more smoothly progress the reaction of at least one compound selected from the group consisting of the dihalosuccinic acid compound (1) and the compound (2) with the nitrophenol compound (3) and thereby to obtain the dicarboxylic acid compound (4) in a higher yield.

The phase transfer catalyst includes, for example, quaternary ammonium chlorides such as tetramethylammonium chloride, tetraethylammonium chloride, tetra(n-propyl)ammonium chloride, tetraisopropylammonium chloride, tetra(n-butyl)ammonium chloride, trimethylbenzylammonium chloride, or triethylbenzylammonium chloride; quaternary ammonium bromides such as tetramethylammonium bromide, tetraethylammonium bromide, tetra(n-propyl)ammonium bromide, tetraisopropylammonium bromide, tetra(n-butyl)ammonium bromide, trimethylbenzylammonium bromide or triethylbenzylammonium bromide; and quaternary ammonium iodides such as tetramethylammonium iodide, tetraethylammonium iodide, tetra(n-propyl)ammonium iodide, tetraisoproyylammonium iodide, tetra(n-butyl) ammonium iodide, trimethylbenzylammonium iodide or triethylbenzylammonium iodide.

The amount used of the phase transfer catalyst is usually 0.005 to 0.5 mole, preferably 0.01 to 0.2 mole per 1 mole of either one of the nitrophenol compound (3) and at least one compound selected from the group consisting of the dihalosuccinic acid compound (1) and the compound (2), wherein the one is used in a smaller amount than the amount used of the other.

After completion of the reaction, a reaction solution containing the dicarboxylic acid compound (4) is obtained. For example, the reaction solution can be separated by adding water and, if necessary, a water-insoluble organic solvent to the reaction solution or by adding the reaction solution to water and, if necessary, a water-insoluble organic solvent, to obtain an organic layer. The organic layer thus obtained can be then concentrated to isolate the dicarboxylic acid compound (4), which can be used for a reaction with acid. The isolated dicarboxylic acid compound (4) may be used after further purification by a conventional purification means. The organic layer containing the dicarboxylic acid compound (4) obtained by separation of the reaction solution as described above may be also used as it is or after washing.

The above-mentioned reaction solution may be also used as it is or in the case of containing insoluble matters, after removing the insoluble matters by filtration or the like if necessary.

With respect to the dicarboxylic acid compound (4), there are two geometrical isomers: a maleic acid compound wherein a group represented by $—CO_2R^1$ and a group represented by $—CO_2R^2$ are positioned on the same side of the carbon-carbon double bond and a fumaric acid compound wherein these groups are positioned on the opposite side. In the present invention, either one of the two geometrical isomers may be used or a mixture of the two geometrical isomers in an optional ratio may be used. The carboxylic acid ester group of the dicarboxylic acid compound (4) may be hydrolyzed with alkali to obtain carboxylic acid and said carboxylic acid may be then subjected to reaction with acid. The conversion into carboxylic acid may be carried out according to a known method (e.g. Aust. J. Chem., 48, 677(1995)).

Such a dicarboxylic acid compound (4') includes, for example, 2-(2-nitrophenoxy)fumaric acid, 2-(2-nitrophenoxy)maleic acid, 2-(3-nitrophenoxy)fumaric acid, 2-(3-nitrophenoxy)maleic acid, 2-(4-nitrophenoxy)fumaric acid, 2-(4-nitrophenoxy)maleic acid, dimethyl 2-(2-nitrophenoxy)fumarate, dimethyl 2-(2-nitrophenoxy)maleate, dimethyl 2-(3-nitrophenoxy)fumarate, dimethyl 2-(3-nitrophenoxy)maleate, dimethyl 2-(4-nitrophenoxy)fumarate, dimethyl 2-(4-nitrophenoxy)maleate, diethyl 2-(2-nitrophenoxy)fumarate, diethyl 2-(2-nitrophenoxy)maleate, diethyl 2-(3-nitrophenoxy)fumarate, diethyl 2-(3-nitrophenoxy)maleate, diethyl 2-(4-nitrophenoxy)fumarate, diethyl 2-(4-nitrophenoxy)maleate, di(n-propyl) 2-(2-nitrophenoxy)fumarate, di(n-propyl) 2-(2-nitrophenoxy)maleate, di(n-propyl) 2-(3-nitrophenoxy)fumarate, di(n-propyl) 2-(3-nitrophenoxy)maleate, di(n-propyl) 2-(4-nitrophenoxy)fumarate, di(n-propyl) 2-(4-nitrophenoxy)maleate, di(n-butyl) 2-(2-nitrophenoxy)fumarate, di(n-butyl) 2-(2-nitrophenoxy)maleate, di(n-butyl) 2-(3-nitrophenoxy)fumarate, di(n-butyl) 2-(3-nitrophenoxy)maleate, di(n-butyl) 2-(4-nitrophenoxy)fumarate, di(n-butyl) 2-(4-nitrophenoxy)maleate, di(tert-butyl) 2-(2-nitrophenoxy)fumarate, di(tert-butyl) 2-(2-nitrophenoxy)maleate, di(tert-butyl) 2-(3-nitrophenoxy)fumarate, di(tert-butyl) 2-(3-nitrophenoxy)maleate, di(tert-butyl) 2-(4-nitrophenoxy)fumarate, di(tert-butyl) 2-(4-nitrophenoxy)maleate, di(n-hexyl) 2-(2-nitrophenoxy)fumarate, di(n-hexyl) 2-(2-nitrophenoxy)maleate, di(n-hexyl) 2-(3-nitrophenoxy)fumarate, di(n-hexyl) 2-(3-nitrophenoxy)maleate, di(n-hexyl) 2-(4-nitrophenoxy)fumarate, and di(n-hexyl) 2-(4-nitrophenoxy)maleate, and these may be used alone or as a mixture of two or more of these.

Next, the process for producing the nitrochromone compound represented by the formula (5) (hereinafter, referred as the nitrochromone compound (5)) by reacting the dicarboxylic acid compound (4') with an acid will be explained.

The acid includes, for example, fuming sulfuric acid, concentrated sulfuric acid, methanesulfonic acid, trifluoromethanesulfonic acid and chlorosulfonic acid and these acids may be used alone or as a mixture of two or more of them. Among them, chlorosulfonic acid is preferred.

The amount used of such an acid is usually 1 part by weight or more per 1 part by weight of the dicarboxylic acid compound (4'). There is no upper limit of the amount and however, in consideration of volume efficiency or economical efficiency, it is practically 50 parts by weight or less per 1 part by weight of the dicarboxylic acid compound (4'). In addition, when the reaction solution containing the dicarboxylic acid compound (4') obtained by reaction of at least compound selected from the group consisting of the compound (1) and the compound (2) with the nitrophenol compound (3) as described above is used as it is, the amount used of the acid may be determined in consideration of the amount of an acid to be used for neutralizing the base remaining in the reaction solution.

The reaction of the dicarboxylic acid compound (4') and the acid may be carried out by mixing and contacting them with each other and the order of mixing them is not particularly limited.

The reaction of the dicarboxylic acid compound (4') and the acid is usually carried out without using a solvent, and however, the reaction may be also carried out in the presence of an organic solvent. The organic solvent is not particularly limited as long as it does not react with an acid.

The reaction temperature varies depending on the type of the acid to be used and it is usually 0 to 150° C., preferably 50 to 120° C.

After completion of the reaction, the resulting reaction solution containing the nitrochromone compound (5) can be usually mixed with water to isolate the nitrochromone compound (5) as a crystal.

Alternatively, the reaction solution containing the nitrochromone compound (5) can be mixed with water, and then a water-insoluble organic solvent if necessary, to carry out extraction and the organic layer thus obtained can be concentrated to isolate the nitrochromone compound (5). The water-insoluble organic solvent includes, for example, aromatic hydrocarbon solvents such as toluene or xylene; ester solvents such as ethyl acetate; aliphatic hydrocarbon solvents such as hexane or heptane; and halogenated hydrocarbon solvents such as dichloromethane or chlorobenzene.

Although the amount used of water is not particularly limited, it is usually 0.5 to 100 parts by weight per 1 part by weight of the dicarboxylic acid compound. In consideration of the volume efficiency or economical efficiency, it is practically 1 to 20 parts by weight per 1 part by weight of the dicarboxylic acid compound.

A method of mixing the reaction solution containing the nitrochromone compound (5) with water may be any method capable of mixing and contacting them with each other. Although the order of mixing them is not particularly limited, in terms of easy control of heat generation caused by mixing, it is preferable to add the reaction solution containing the nitrochromone compound (5) to water.

As water to be used, an aqueous salt solution containing an inorganic salt such as sodium chloride, sodium bromide, potassium chloride, potassium bromide, lithium chloride, lithium bromide, calcium chloride or sodium sulfate may be used. The concentration of the inorganic salt is in the range from 0% by weight to the saturated solubility and is not particularly limited.

The temperature for mixing the reaction solution containing the nitrochromone compound (5) with water is in the range from above the solidifying point to the reflux temperature of the system and is not particularly limited. In order to obtain the carboxylic acid ester of the formula (5), the reaction solution and water are preferably mixed under cooling, for example, at 0° C. or lower, so that the compound represented by the formula (5) can be mainly obtained as carboxylic acid ester.

The crystal of the reaction product precipitated after the mixing can be obtained usually as a solid by filtration.

From the dicarboxylic acid compound represented by the formula (4') in which $R^{10}$ is hydrogen, the nitrochromone compound represented by the formula (5) in which $R^{10}$ is hydrogen is obtained. From the dicarboxylic acid compound represented by the formula (4') in which $R^{10}$ is a lower alkyl group, the carboxylic acid ester compound of the nitrochromone compound represented by the formula (5) in which $R^{10}$ is a lower alkyl group is obtained. Further, the group —$CO_2R^{10}$ at the 2-position of said carboxylic acid ester compound is hydrolyzed by the above-mentioned treatment to produce nitrochromone carboxylic acid having the carboxyl group —$CO_2H$ at the 2-position or a mixture of the above-mentioned carboxylic acid ester compound and said carboxylic acid. The carboxylic acid ester compound or carboxylic acid of the nitrochromone compound thus obtained or a mixture thereof may be subjected to recrystallization or extraction to purify or isolate the carboxylic acid eater or carboxylic acid of the nitrochromone compound, if necessary. By the following method, the carboxylic acid of the nitrochromone compound of the formula (5) thus obtained or a mixture of the carboxylic acid compound and the carboxylic acid ester compound can be reacted with an alkylating agent in the presence of a base to esterify the carboxyl group of the nitrochromone compound. A method for the esterification is not particularly limited as long as it is a method for synthesizing ester from carboxylic acid. It may be a known method, for example, described in Jikken Kagaku Koza vol. 22, 4th Ed., the Chemical Society of Japan, p. 43; Shin Jikken Kagaku Koza vol. 14, the Chemical Society of Japan p. 1002; or Comprehensive Organic Functional Group Transformations, PERGAMON(1995) vol. 5, p. 121.

Preferred methods are, for example, a method for esterification by reacting with lower alcohol represented by $R^1OH$ or $R^2OH$ (wherein $R^1$ and $R^2$ are as defined above) in the presence of an acid catalyst; a method for esterification by reacting with alcohol via carboxylic acid chloride; and a method for esterification by using a suitable alkylating agent [e.g. the formula $R^1$-L (wherein $R^1$ is as defined above, L represents a leaving group such as a halogen atom or aryl-(phenyl or tosyl), alkyl- or haloalkylsulfonyloxy)] in the presence of an organic base in an aprotic organic solvent.

The method for esterification by using an alkylating agent in the presence of an organic base in an aprotic organic solvent is preferably employed. This method will be explained in details below.

The aprotic organic solvent includes, for example, aprotic polar solvents such as N,N-dimethylformamide, N-methylpyrrolidone, 1,3-dimethyl-2-imidazolidinone, dimethyl sulfoxide, sulfolane, acetonitrile or propionitrile; ketone solvents such as acetone or methyl isobutyl ketone; aromatic hydrocarbon solvents such as toluene or xylene; halogenated hydrocarbon solvents such as dichloromethane, dichloroethane, chlorobenzene or dichlorobenzene; ether solvents such as dimethyl ether, methyl tert-butyl ether or tetrahydrofuran; and ester solvents such as ethyl acetate and these solvents may be used alone or as a mixture of two or more of these. Preferably, aromatic hydrocarbon solvents or ester solvents are used alone or as a mixture of two or more of them. The amount used of the solvent is usually 1 to 50 parts by weight per 1 part by weight of the nitrochromone carboxylic acid mixture.

The organic base includes, for example, tertiary amines such as triethylamine, tributylamine, diisopropylethylamine or 1, 8-diazabicyclo[5.4.0]undeca-7-ene; and pyridine compounds such as pyridine or 5-ethyl-2-methylpyridine, and these bases may be used alone or as a mixture of two or more of these. Among them, aliphatic tertiary amines are preferred.

Although the amount used of the organic base is not particularly limited, it is usually 0.8 to 5 moles, preferably 0.9 to 3 moles per 1 mole of the nitrochromone compound (5) in which $R^{10}$ is hydrogen because use of too much organic base results in economic disadvantage and difficulty in purification.

The alkylating agent includes, for example, alkyl halides such as methyl chloride, ethyl chloride, propyl chloride, butyl chloride, methyl bromide, ethyl bromide, propyl bromide, butyl bromide, isobutyl bromide, isopropyl bromide, pentyl bromide, hexyl bromide, methyl iodide, ethyl iodide, pentyl iodide, isobutyl iodide, isopropyl iodide, pentyl iodide, hexyl iodide, butyl iodide, propyl iodide, heptyl iodide, or hexyl iodide; sulfonic acid alkyl esters such as methanesulfonic acid alkyl ester, chloromethanesulfonic acid alkyl ester, p-toluenesulfonic acid alkyl ester, trifluoromethanesulfonic acid alkyl ester, nonafluorobutanesulfonic acid alkyl ester (wherein the alkyl group includes methyl, ethyl, propyl, butyl, isopropyl and isobutyl); and dialkyl sulfate such as diethyl sulfate or dimethyl sulfate. Among them, dialkyl sulfate is preferred.

Although the amount used of the alkylating agent is not particularly limited, it is usually about 0.8 to 5 moles, preferably about 0.9 to 3 moles per 1 mole of the nitrochromone carboxylic acid because use of too much alkylating agent results in economic disadvantage and difficulty in purification.

Although the temperature for the esterification is not particularly limited, it is in the range from above the solidifying point to the reflux temperature of the system, preferably about 10 to 100° C. By such methods, nitrochromone compound esters having ester groups suitable to the purposes can be produced.

The nitrochromone compound (5) thus obtained includes, for example, 5-nitro-2-carboxy-4-oxo-4H-1-benzopyran, 6-nitro-2-carboxy-4-oxo-4H-1-benzopyran, 7-nitro-2-carboxy-4-oxo-4H-1-benzopyran, 8-nitro-2-carboxy-4-oxo-4H-1-benzopyran, 5-nitro-2-methoxycarbonyl-4-oxo-4H-1-benzopyran, 6-nitro-2-methoxycarbonyl-4-oxo-4H-1-benzopyran, 7-nitro-2-methoxycarbonyl-4-oxo-4H-1-benzopyran, 8-nitro-2-methoxycarbonyl-4-oxo-4H-1-benzopyran, 5-nitro-2-ethoxycarbonyl-4-oxo-4H-1-benzopyran, 6-nitro-2-ethoxycarbonyl-4-oxo-4H-1-benzopyran, 7-nitro-2-ethoxycarbonyl-4-oxo-4H-1-benzopyran, 8-nitro-2-ethoxycarbonyl-4-oxo-4H-1-benzopyran, 5-nitro-2-(n-propoxycarbonyl)-4-oxo-4H-1-benzopyran, 6-nitro-2-(n-propoxycarbonyl)-4-oxo-4H-1-benzopyran, 7-nitro-2-(n-propoxycarbonyl)-4-oxo-4H-1-benzopyran, 8-nitro-2-(n-propoxycarbonyl)-4-oxo-4H-1-benzopyran, 5-nitro-2-isopropoxycarbonyl-4-oxo-4H-1-benzopyran, 6-nitro-2-isopropoxycarbonyl-4-oxo-4H-1-benzopyran, 7-nitro-2-isopropoxycarbonyl-4-oxo-4H-1-benzopyran, 8-nitro-2-isopropoxycarbonyl-4-oxo-4H-1-benzopyran, 5-nitro-2-(n-butoxycarbonyl)-4-oxo-4H-1-benzopyran, 6-nitro-2-(n-butoxycarbonyl)-4-oxo-4H-1-benzopyran, 7-nitro-2-(n-butoxycarbonyl)-4-oxo-4H-1-benzopyran, 8-nitro-2-(n-butoxycarbonyl)-4-oxo-4H-1-benzopyran, 5-nitro-2-isobutoxycarbonyl-4-oxo-4H-1-benzopyran, 6-nitro-2-isobutoxycarbonyl-4-oxo-4H-1-benzopyran, 7-nitro-2-isobutoxycarbonyl-4-oxo-4H-1-benzopyran, 8-nitro-2-isobutoxycarbonyl-4-oxo-4H-1-benzopyran, 5-nitro-2-(tert-butoxycarbonyl)-4-oxo-4H-1-benzopyran, 6-nitro-2-(tert-butoxycarbonyl)-4-oxo-4H-1-benzopyran, 7-nitro-2-(tert-butoxycarbonyl)-4-oxo-4H-1-benzopyran, 8-nitro-2-(tert-butoxycarbonyl)-4-oxo-4H-1-benzopyran, 5-nitro-2-(n-pentyloxycarbonyl)-4-oxo-4H-1-benzopyran, 6-nitro-2-(n-pentyloxycarbonyl)-4-oxo-4H-1-benzopyran, 7-nitro-2-(n-pentyloxycarbonyl)-4-oxo-4H-1-benzopyran, 8-nitro-2-(n-pentyloxycarbonyl)-4-oxo-4H-1-benzopyran, 5-nitro-2-(n-hexyloxycarbonyl)-4-oxo-4H-1-benzopyran, 6-nitro-2-(n-hexyloxycarbonyl)-4-oxo-4H-1-benzopyran, 7-nitro-2-(n-hexyloxycarbonyl)-4-oxo-4H-1-benzopyran, and 8-nitro-2-(n-hexyloxycarbonyl)-4-oxo-4H-1-benzopyran.

Next, a step of reducing the nitrochromone compound to obtain an aminochromone compound will be explained.

The metal species of a metal catalyst used in the present invention includes, for example, late transition metals such as palladium, platinum, nickel, rhodium, ruthenium, iridium or cobalt. The metal catalyst includes, for example, heterogeneous metal catalysts, wherein the metal species is supported on a carrier such as activated carbon, silica or alumina, such as palladium/carbon, platinum/carbon, rhodium/carbon, ruthenium/carbon, palladium/silica or palladium/alumina and homogeneous metal catalysts such as chlorotris(triphenylphosphine)rhodium, tetrakis(triphenylphosphine)palladium, palladium acetate, dichlorotris (triphenylphosphine)ruthenium, tetrakis(triphenylphosphine)platinum or tetrakis(triphenylphosphine)nickel.

The amount used of such a metal catalyst is usually 0.00001 to 0.01 parts by weight on the basis of metal weight per 1 part by weight of the nitrochromone compound (5).

The base includes, for example, alkali metal hydroxide such as sodium hydroxide; alkaline earth metal hydroxide such as calcium hydroxide; alkali metal carbonate such as lithium carbonate, sodium carbonate or potassium carbonate; alkaline earth metal carbonate such as calcium carbonate; alkali metal hydrogen carbonate such as sodium hydrogen carbonate or potassium hydrogen carbonate; alkali metal monohydrogenphosphate such as sodium monohydrogenphosphate; alkali metal phosphate such as sodium phosphate; alkali metal carboxylate such as sodium acetate, lithium acetate, potassium acetate, sodium propionate, sodium benzoate, sodium oxalate, sodium malonate, or sodium tartrate; tertiary amine such as triethylamine, tri(n-butyl)amine, dimethylaniline, N-methylpyrrolidine, or N-methylmorpholine; and pyridine compounds such as pyridine, 2-methylpyridine, 2-methyl-5-ethylpyridine, or 4-dimethylaminopyridine, and among them, preferred are alkali metal carbonate, alkali metal hydrogen carbonate, alkali metal carboxylate, tertiary amine and pyridine compounds. Such bases may be used alone or as a mixture of two or more of them and may be used as they are or as a mixture with the above-mentioned organic solvent or water.

The amount used of the base is usually 0.01 mole or more per 1 mole of the nitrochromone compound (5) and there is no upper limit thereof. For example, if the base is in the liquid form under the reaction condition, it may be used both as a base and a reaction solvent in a considerably excess amount. However, in consideration of the cost, the amount used of the base is practically 5 moles or less per 1 mole of the nitrochromone compound (5).

The reaction temperature is usually 0 to 100° C. The amount used of hydrogen is usually 3 moles or more per 1 mole of the nitrochromone compound (5) and the upper limit is not particularly limited.

The reaction may be carried out under the normal pressure or a pressurized condition. When the reaction is carried out under a pressurized condition, the pressurized condition is preferably 5 MPa or lower in consideration of a practical aspect.

The reaction is usually carried out in the presence of an organic solvent. The organic solvent includes, for example, aprotic polar solvents such as N,N-dimethylformamide; alcohol solvents such as methanol or ethanol; aromatic hydrocarbon solvents such as toluene or xylene; halogenated hydrocarbon solvents such as dichloromethane, dichloroethane, chlorobenzene or dichlorobenzene; ether solvents such as dimethyl ether, methyl tert-butyl ether or tetrahydrofuran; and ester solvents such as ethyl acetate and these solvents may be used alone or as a mixture of two or more of these. Further, when the base used is in the liquid form under the reaction condition, the base may be used as a solvent. The amount used of the solvent is usually 2 to 50 parts by weight per 1 part by weight of the nitrochromone compound (5).

When a heterogeneous metal catalyst is used, the heterogeneous metal catalyst is usually removed from a reaction solution by filtration to obtain a solution containing the aminochromone compound represented by the formula (6) wherein $R^{10}$ represents a hydrogen atom or a $C_{1-6}$ alky group (hereinafter, referred as the aminochromone compound (6)) and the solution can be concentrated to isolate the aminochromone compound (6). Alternatively, the aminochromone compound (6) can be crystallized from the solution. A method for the crystallization includes, for example, cooling of the above-mentioned solution and mixing of the above-mentioned solution with an insufficient solvent.

In the process of the present invention, byproduction of over-reduced compounds is suppressed, so that the aminochromone compound (6) with a high purity can be isolated. The isolated aminochromone compound (6) may be further purified by a conventional purification means such as recrystallization. In addition, in a step of removing the above-mentioned heterogeneous metal catalyst, acid may be added. The acid includes, for example, mineral acid such as hydrochloric acid, sulfuric acid or phosphoric acid and organic acid such as formic acid or acetic acid. The amount added of the acid is usually 0.1 to 3 moles per 1 mole of the base used. When acid is added for removal of the heterogeneous metal catalyst, depending on the amount added of the acid, a mixture of the aminochromone compound (6) and an acid addition salt of the aminochromone compound (6), or an acid addition salt of the aminochromone compound (6) alone may be obtained. When the homogeneous metal catalyst is used, the aminochromone compound (6) may be isolated, for example, by crystallization from a reaction solution, or by flocculation and filtration of the catalyst in a reaction solution and then concentration or crystallization of the filtrate.

The aminochromone compound (6) thus obtained includes, for example, 5-amino-2-carboxy-4-oxo-4H-1-benzopyran, 6-amino-2-carboxy-4-oxo-4H-1-benzopyran, 7-amino-2-carboxy-4-oxo-4H-1-benzopyran, 8-amino-2-carboxy-4-oxo-4H-1-benzopyran, 5-amino-2-methoxycarbonyl-4-oxo-4H-1-benzopyran, 6-amino-2-methoxycarbonyl-4-oxo-4H-1-benzopyran, 7-amino-2-methoxycarbonyl-4-oxo-4H-1-benzopyran, 8-amino-2-methoxycarbonyl-4-oxo-4H-1-benzopyran, 5-amino-2-ethoxycarbonyl-4-oxo-4H-1-benzopyran, 6-amino-2-ethoxycarbonyl-4-oxo-4H-1-benzopyran, 7-amino-2-ethoxycarbonyl-4-oxo-4H-1-benzopyran, 8-amino-2-ethoxycarbonyl-4-oxo-4H-1-benzopyran, 5-amino-2-(n-propoxycarbonyl)-4-oxo-4H-1-benzopyran, 6-amino-2-(n-propoxycarbonyl)-4-oxo-4H-1-benzopyran, 7-amino-2-(n-propoxycarbonyl)-4-oxo-4H-1-benzopyran, 8-amino-2-(n-propoxycarbonyl)-4-oxo-4H-1-benzopyran, 5-amino-2-isopropoxycarbonyl-4-oxo-4H-1-benzopyran, 6-amino-2-isopropoxycarbonyl-4-oxo-4H-1-benzopyran, 7-amino-2-isopropoxycarbonyl-4-oxo-4H-1-benzopyran, 8-amino-2-isopropoxycarbonyl-4-oxo-4H-1-benzopyran, 5-amino-2-(n-butoxycarbonyl)-4-oxo-4H-1-benzopyran, 6-amino-2-(n-butoxycarbonyl)-4-oxo-4H-1-benzopyran, 7-amino-2-(n-butoxycarbonyl)-4-oxo-4H-1-benzopyran, 8-amino-2-(n-butoxycarbonyl)-4-oxo-4H-1-benzopyran, 5-amino-2-isobutoxycarbonyl-4-oxo-4H-1-benzopyran, 6-amino-2-isobutoxycarbonyl-4-oxo-4H-1-benzopyran, 7-amino-2-isobutoxycarbonyl-4-oxo-4H-1-benzopyran, 8-amino-2-isobutoxycarbonyl-4-oxo-4H-1-benzopyran, 5-amino-2-(tert-butoxycarbonyl)-4-oxo-4H-1-benzopyran, 6-amino-2-(tert-butoxycarbonyl)-4-oxo-4H-1-benzopyran, 7-amino-2-(tert-butoxycarbonyl)-4-oxo-4H-1-benzopyran, 8-amino-2-(tert-butoxycarbonyl)-4-oxo-4H-1-benzopyran, 5-amino-2-(n-pentyloxycarbonyl)-4-oxo-4H-1-benzopyran, 6-amino-2-(n-pentyloxycarbonyl)-4-oxo-4H-1-benzopyran, 7-amino-2-(n-pentyloxycarbonyl)-4-oxo-4H-1-benzopyran, 8-amino-2-(n-pentyloxycarbonyl)-4-oxo-4H-1-benzopyran, 5-amino-2-(n-hexyloxycarbonyl)-4-oxo-4H-1-benzopyran, 6-amino-2-(n-hexyloxycarbonyl)-4-oxo-4H-1-benzopyran, 7-amino-2-(n-hexyloxycarbonyl)-4-oxo-4H-1-benzopyran, and 8-amino-2-(n-hexyloxycarbonyl)-4-oxo-4H-1-benzopyran.

The aminochromone compound (6) (wherein, preferably, $R^{10}$ represents a lower alkyl group) obtained according to the present invention can be acylated using a reactive derivative of carboxylic acid represented by the formula (7): $R^{11}COZ$ (wherein $R^{11}$ represents a substituted or unsubstituted aliphatic group or a substituted or unsubstituted aromatic group and Z represents a leaving group such as a halogen atom or an acyloxy group) to obtain the corresponding amidochromone compound.

The reaction is usually carried out in the presence of an organic solvent. The organic solvent includes, for example, aprotic polar solvents such as N,N-dimethylformamide, aromatic hydrocarbon solvents such as toluene or xylene, halogenated hydrocarbon solvents such as dichloromethane, dichloroethane, chlorobenzene or dichlorobenzene, ether solvents such as dimethyl ether, methyl tert-butyl ether or tetrahydrofuran, nitrile solvents such as acetonitrile or propionitrile, and ester solvents such as ethyl acetate, and these solvents may be used alone or as a mixture of two or more of these. The amount used of the solvent is usually 2 to 50 parts by weight per 1 part by weight of the aminochromone compound.

The reactive derivative of carboxylic acid represented by the formula (7) includes specifically, for example, substituted or unsubstituted aliphatic or aromatic carboxylic acid halides such as acetic acid chloride, benzoic acid chloride or 4-(4-phenylbutoxy)benzoic acid chloride and acid anhydrides such as acetic anhydride or benzoic anhydride. The activated derivative of carboxylic acid can be also obtained by using aliphatic or aromatic carboxylic acid and a carboxylic acid activating agent (e.g. 1,3-dicyclohexylcarbodiimide).

The reaction of the aminochromone compound (6) with the reactive derivative of carboxylic acid represented by the formula (7) may be carried out by adding the reactive derivative of carboxylic acid or a mixture of the reactive derivative and an organic solvent into a mixture of the aminochromone compound (6) and an organic solvent, by adding the aminochromone compound (6) or a mixture of the aminochromone compound (6) and an organic solvent into the reactive derivative of carboxylic acid or a mixture of the reactive derivative and an organic solvent, or by adding the aminochromone compound (6) and the reactive derivative of carboxylic acid simultaneously.

In the above-mentioned reaction, addition of a base may be effective if necessary. The base includes, for example, alkali metal hydroxide such as lithium hydroxide, sodium hydroxide or potassium hydroxide; alkaline earth metal hydroxide such as calcium hydroxide or barium hydroxide; alkali metal carbonate such as lithium carbonate, sodium carbonate or potassium carbonate; alkaline earth metal carbonate such as calcium carbonate; alkali metal hydrogen carbonate such as sodium hydrogen carbonate or potassium hydrogen carbonate; and organic amines such as triethylamine, pyridine or 5-ethyl-2-methylpyridine, and these may be used alone or as a mixture of two or more of these. The base may be added as it is to a reaction solution or if it is water-soluble, it may be added to a reaction solution after dissolving. If the base is in liquid form, it may be used also as a solvent.

Although the upper limit of the reaction temperature may be determined depending on the boiling point of a solvent used, it is usually –50° C. to 150° C., preferably –20° C. to 100° C.

After completion of the reaction, the desired amidochromone compound can be produced by a conventional separation means, for example, filtration, solvent extraction, or concentration. The amidochromone compound thus obtained may be further purified by, for example, recrystallization if necessary.

Thus, the aminochromone compound (6) can be converted into the amidochromone compound represented by the formula (8), which is a pharmaceutical intermediate, for example, as described in JP-A 3-95144.

The amidochromone compound represented by the formula (8) which is obtained from the aminochromone compound (6) (wherein $R^{10}$ represents a lower alkyl group) can be subjected to a step of reacting with ammonia to convert into carbamoyl and then to a step of dehydrating the resulting compound having carbamoyl to produce the amidochromonenitrile compound represented by the formula (10), as described in the following reaction scheme-1. Such a series of reaction steps can be carried out according to a known method described in, for example, JP-A 3-95144, JP-A 61-50977 or EP 634409A. For example, the conversion of the compound represented by the formula (8) into the compound represented by the formula (9) can be carried out using ammonia in an inert solvent (e.g. lower alkyl alcohol, the above-mentioned aromatic hydrocarbon solvents, halogenated hydrocarbon solvents, ether solvents, or aprotic polar solvents). The step of dehydrating the compound represented by the formula (9) to obtain the compound represented by the formula (10) can be carried out using a dehydrating agent such as phosphorus oxychloride or thionyl chloride. The dehydration step may be carried out using an inert organic solvent (e.g. aromatic hydrocarbon, halogenated hydrocarbon solvents, ether solvents, or aprotic polar solvents) if necessary.

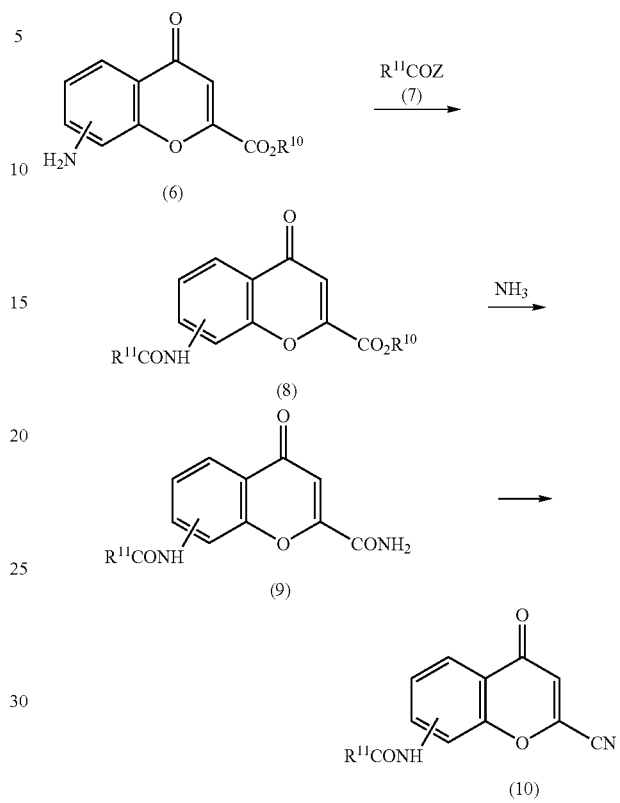

Reaction Scheme-1

EXAMPLES

Hereinafter, the present invention will be explained more specifically with reference to Examples, which are not intended to limit the scope of the present invention. The yield and the ratio between stereoisomers were calculated from results of high performance liquid chromatography.

Example 1

A reaction container equipped with a stirrer, a cooling tube and a thermometer was charged with 1,883 parts by weight of bromine at room temperature and adjusted to an inner temperature of 30° C. At an inner temperature of 30 to 40° C., 1,544 parts by weight of dimethyl maleate was added dropwise over 4 hours to the content and the mixture was stirred and kept at an inner temperature of 40° C. for 4 hours to react it. After that, at room temperature, the reaction solution was added dropwise slowly to 2,228 parts by weight of a 10% by weight sodium sulfite aqueous solution. After the mixture was stirred until brown color showing residual bromine disappeared, 4,884 parts by weight of toluene was added thereto to separate the solution. The obtained organic layer was washed with 1,249 parts by weight of a 10% by weight sodium carbonate aqueous solution and then with 2,228 parts by weight of water, and then concentrated under reduced pressure to obtain 3,179 parts by weight of dimethyl dibromosuccinate as white crystals. The content was 98.4% by weight, the yield was 97%, and the threo/erythro ratio was 98/2.

Example 2

A reaction container equipped with a stirrer, a cooling tube and a thermometer was charged with 36.3 parts by weight of chlorobenzene at room temperature and 34.3 parts by weight of bromine was added dropwise thereto. After the container was adjusted to an inner temperature of 50° C., 28.1 parts by weight of dimethyl maleate was added dropwise over 1 hour thereto and the content was stirred and kept at 50° C. for 5 hours to react it. After that, at room temperature, the reaction solution was added dropwise slowly to 38 parts by weight of a 10% by weight sodium sulfite aqueous solution. The mixture was stirred until brown color showing residual bromine disappeared and then separated. The obtained organic layer was washed with 30 parts of 10% by weight sodium carbonate aqueous solution and then with 30 parts by weight of water to obtain an organic layer containing 56.3 parts by weight of dimethyl dibromosuccinate. The yield was 95% and the threo/erythro ratio was 98/2.

Example 3

A reaction container equipped with a stirrer, a cooling tube and a thermometer was charged with 25.0 parts by weight of bromine at room temperature and adjusted to an inner temperature of 40° C. At an inner temperature of 40 to 45° C., 20.5 parts by weight of dimethyl maleate was added dropwise over 10 hours thereto and the content was stirred and kept at an inner temperature of 40° C. for 2 hours to react it. After that, at room temperature, the reaction solution was added dropwise slowly to 24.2 parts by weight of 10% by weight sodium sulfite aqueous solution. After the mixture was stirred until brown color showing residual bromine disappeared, 61.7 parts by weight of toluene was added thereto to separate the solution. The obtained organic layer was mixed with 20.5 parts by weight of an 18% solution of sodium chloride in water and adjusted to pH 5.4 with a 10% by weight sodium carbonate aqueous solution. The organic layer was then washed with 20.5 parts by weight of water and concentrated under reduced pressure to obtain 51.9 parts by weight of a solution of dimethyl dibromosuccinate in toluene. The content was 80.0% by weight, the yield was 96% and the threo/erythro ratio was 99/1.

Comparative Example 1

A reaction container equipped with a stirrer, a cooling tube and a thermometer was charged with 28.1 parts by weight of dimethyl maleate at room temperature and adjusted o an inner temperature of 50° C. After 34.3 parts by weight of bromine was added dropwise at 50° C. over 2 hours thereto, the content was stirred and kept at the same temperature for 6 hours to react it. After that, the reaction solution was added dropwise slowly to 38 parts by weight of a 10% by weight sodium sulfite aqueous solution at room temperature. After the mixture was stirred until brown color showing residual bromine disappeared, 90 parts by weight of toluene was added thereto to separate the solution. The obtained organic layer was washed with 30 parts by weight of a 10% by weight sodium carbonate aqueous solution and then with 30 parts by weight of water to obtain an organic layer containing 56.6 parts by weight of dimethyl dibromosuccinate. The yield was 96% and the threo/erythro ratio was 62/38.

Example 4

A reaction container equipped with a stirrer, a cooling tube and a thermometer was charged with 60 parts by weight of toluene, 20 parts by weight of sulfolane and then 20 parts by weight of 2-nitrophenol at room temperature, and thereto 60 parts by weight of potassium carbonate was added in small portions. The inner temperature was raised to 100° C. and the content was stirred and kept at the same temperature for 1 hour. After cooled to an inner temperature of 80° C., to the content, 4.7 parts by weight of tetra(n-butyl)ammonium bromide was added and a mixture of 50 parts by weight of dimethyl erythro-2,3-dibromosuccinate and 40 parts by weight of toluene was then added dropwise over 4 hours. The mixture was stirred and kept at an inner temperature of 80° C. for 7 hours to react it. The reaction solution was cooled to room temperature and 180 parts by weight of water was added thereto to separate the solution. The obtained organic layer was washed with a 5% by weight sodium hydrogen carbonate aqueous solution and then with a 5% by weight solution of sodium chloride in water and then concentrated under reduced pressure to obtain 42.4 parts by weight of an oil containing dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 82.0% by weight, and the yield based on 2-nitrophenol was 86.1%.

$^1$H-NMR spectra for dimethyl 2-(2-nitrophenoxy)fumarate (DMSO-$d_6$ solvent, TMS standard, unit: ppm) δ 8.16 (1H, d), 7.85(1H, t), 7.55(1H, t), 7.50(1H, d), 5.56(1H, s), 3.82(3H, s), 3.64(3H, s)

$^1$H-NMR spectra for dimethyl 2-(2-nitrophenoxy)maleate (DMSO-$d_6$ solvent, TMS standard, unit: ppm) δ 8.05(1H, d), 7.65(1H, t), 7.34(1H, t), 7.20(1H, d), 6.80(1H, s), 3.74(3H, s), 3.68(3H, s)

Example 5

A reaction container equipped with a stirrer, a cooling tube and a thermometer was charged with 9 parts by weight of toluene, 3 parts by weight of N,N-dimethylformamide and then 3 parts by weight of 2-nitrophenol at room temperature. Thereto, 8.9 parts by weight of potassium carbonate was added in small portions. The inner temperature was raised to 100° C. and the content was stirred and kept at the same temperature for 1 hour. After cooled to an inner temperature of 80° C., to the content, 0.7 parts by weight of tetra(n-butyl)ammonium bromide was added and a mixture of 7 parts by weight of dimethyl erythro-2,3-dibromosuccinate and 6 parts by weight of toluene was then added dropwise over 2 hours. The mixture was stirred and kept at an inner temperature of 80° C. for 6 hours to react it. After the reaction solution was cooled to room temperature, 40 parts by weight of water was added thereto to separate the solution. The obtained organic layer contained dimethyl 2-(2-nitrophenoxy)fumarate and dimethyl 2-(2-nitrophenoxy)maleate. The combined amount of dimethyl 2-(2-nitrophenoxy)fumarate and dimethyl 2-(2-nitrophenoxy)maleate was 4.4 parts by weight, and the yield based on 2-nitrophenol was 70.8%.

Example 6

A reaction container equipped with a stirrer, a cooling tube and a thermometer was charged with 30 parts by weight of toluene, 2.2 parts by weight of dimethyl erythro-2,3-dibromosuccinate and 1 part by weight of 2-nitrophenol at room temperature. Thereto, 4 parts by weight of potassium carbonate and 0.23 parts by weight of tetra(n-butyl)ammonium bromide were added. The inner temperature was raised to 60° C. and the content was stirred and kept at the same temperature for 5 hours, at an inner temperature of 80° C. for 1 hour and then at an inner temperature of 100° C. for 1 hour to react it. The reaction solution was cooled to room temperature and 30 parts by weight of water was added thereto to separate the solution. The obtained organic layer was washed with a 5% by weight sodium hydrogen carbonate aqueous solution and a 5% by weight solution of sodium chloride in water, and then concentrated under reduced pressure to obtain 1.7 parts by weight of an oil containing dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 90.4% by weight, and the yield based on 2-nitrophenol was 74.3%.

Example 7

A reaction container equipped with a stirrer, a cooling tube and a thermometer was charged with 15 parts by weight of N,N-dimethylformamide, 1.1 parts by weight of dimethyl erythro-2,3-dibromosuccinate and 0.5 parts by weight of 2-nitrophenol at room temperature. Thereto, 2 parts by weight of potassium carbonate was added. The inner temperature was raised to 60° C. and the content was stirred and kept at the same temperature for 5 hours to react it. The reaction solution was cooled to room temperature and 30 parts by weight of water was added thereto to separate the solution. The obtained organic layer was washed with a 5% by weight sodium hydrogen carbonate aqueous solution and then with a 5% by weight solution of sodium chloride in water and then concentrated under reduced pressure to obtain 0.72 parts by weight of an oil containing dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 88.9% by weight, and the yield based on 2-nitrophenol was 63.3%.

Example 8

A reaction container equipped with a stirrer, a cooling tube and a thermometer was charged with 10 parts by weight of toluene, 5.3 parts by weight of dimethyl erythro-2,3-dibromosuccinate and 2 parts by weight of 2-nitrophenol at room temperature. Thereto, 4.6 parts by weight of sodium carbonate and 0.47 parts by weight of tetra(n-butyl)ammonium bromide were added. The inner temperature was raised to 80° C. and the content was stirred and kept at the same temperature for 3 hours and then at an inner temperature of 100° C. for 5 hours to react it. The reaction solution was cooled to room temperature and 20 parts by weight of water and 20 parts by weight of toluene were added thereto to separate the solution. The obtained organic layer was washed with a 5% by weight sodium hydrogen carbonate aqueous solution and then with a 5% by weight solution of sodium chloride in water and then concentrated under reduced pressure to obtain 3.8 parts by weight of an oil containing dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 59.6% by weight, and the yield based on 2-nitrophenol was 55.7%.

Example 9

A reaction container equipped with a stirrer, a cooling tube and a thermometer was charged with 10.5 parts by weight of toluene, 3 parts by weight of sulfolane and then 3 parts by weight of 2-nitrophenol at room temperature. Thereto, 6 parts by weight of potassium carbonate was added in small portions. The inner temperature was raised to 100° C. and the content was stirred and kept at the same temperature for 1 hour. After cooled to an inner temperature of 80° C., to the content, 0.7 parts by weight of tetra(n-butyl)ammonium bromide was added and then a mixture of 7.5 parts by weight of toluene and 5.5 parts by weight of a mixture of dimethyl 2-boromofumarate and dimethyl 2-bromomaleate was added dropwise over 3 hours. The resulting mixture was stirred and kept at an inner temperature of 80° C. for 5 hours to react it. The reaction solution was cooled to room temperature and 21 parts by weight of water was added to separate the solution. The obtained organic layer was washed with a 5% by weight sodium hydrogen carbonate aqueous solution and then with a 5% by weight solution of sodium chloride in water and then concentrated under reduced pressure to obtain 5.8 parts by weight of an oil containing dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 81.4% by weight and the yield based on 2-nitrophenol was 77.7%.

Example 10

A reaction container equipped with a stirrer, a cooling tube and a thermometer was charged with 44.1 parts by weight of toluene, 4.2 parts by weight of sulfolane, 21.1 parts by weight of potassium carbonate and 2.0 parts by weight of tetra(n-butyl)ammonium bromide at room temperature. After the mixture was warmed to 105° C., a mixture of 17.0 part by weight of 2-nitrophenol and 17.3 parts by weight of toluene was added dropwise thereto over 2 hours. The mixture was stirred and kept at 105° C. for 1 hour. After cooled to an inner temperature of 70° C., a mixture of 7.6 parts by weight of toluene and 40.1 parts by weight of a mixture (threo-isomer content: 98.0%) of dimethyl threo-2,3-dibromosuccinate and dimethyl erythro-2,3-dibromosuccinate was added dropwise over 3 hours thereto. The mixture was stirred and kept at an inner temperature of 70° C. for 7 hours to react it. The reaction solution was cooled to room temperature and 51 parts by weight of water was added to separate the solution. The obtained organic layer was washed with a 5% by weight sodium hydrogen carbonate aqueous solution and then with a 5% by weight solution of sodium chloride in water and then concentrated under reduced pressure to obtain 37.8 parts by weight of a mixture (oily) of dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 89.6% by weight and the yield based on 2-nitrophenol was 98.7%.

Example 11

A reaction container equipped with a stirrer, a cooling tube and a thermometer was charged with 100 parts by weight of toluene, 10.0 parts by weight of sulfolane, 49.7 parts by weight of potassium carbonate and 4.7 parts by weight of tetra(n-butyl)ammonium bromide at room temperature. After the mixture was warmed to 95° C., a mixture of 40.1 parts by weight of 2-nitrophenol and 40.1 parts by weight of toluene was added dropwise over 2 hours thereto. The resulting mixture was stirred and kept at 95° C. for 1 hour. After cooled to an inner temperature of 70° C., a mixture of 20.0 parts by weight of toluene and 102.8 parts by weight of a mixture (threo-isomer content: 86.3%) of dimethyl threo-2,3-dibromosuccinate and dimethyl erythro-2,3-dibromosuccinate was added dropwise over 4 hours thereto and the mixture was stirred and kept at the same temperature for 5 hours to react it. The reaction solution was cooled to room temperature and 120 parts by weight of water was added to separate the solution. The obtained organic layer was washed with a 5% by weight sodium hydrogen carbonate aqueous solution and then with a 5% by weight solution of sodium chloride in water and then concentrated under reduced pressure to obtain 93.9 parts by weight of a mixture (oily) of dimethyl 2-(2-nitrophenoxy)fumarate and dimethyl 2-(2-nitrophenoxy)maleate. The combined content of dimethyl 2-(2-nitrophenoxy)fumarate and dimethyl 2-(2-nitrophenoxy)maleate was 83.5% by weight and the yield based on 2-nitrophenol was 96.8%.

Example 12

A reaction container equipped with a stirrer, a cooling tube and a thermometer was charged with 101 parts by weight of toluene, 10.1 parts by weight of sulfolane, 24.9 parts by weight of potassium carbonate, 2.3 parts by weight of tetra(n-butyl)ammonium bromide and 20.0 parts by weight of 4-nitrophenol at room temperature. After warmed to 110° C., the mixture was stirred and kept at the same temperature for 1 hour. After the mixture was cooled to an inner temperature of 70° C., a mixture of 20.0 parts by weight of toluene and 47.1 parts by weight of a mixture (threo-isomer content: 96.0%) of dimethyl threo-2,3-dibromosuccinate and dimethyl erythro-2,3-dibromosuccinate was added dropwise thereto over 2 hours. The resulting mixture was stirred and kept at an inner temperature of 70° C. for 2 hours, at 85° C. for 4 hour, at 95° C. for 3 hour, and then at 105° C. for 3 hours to react it. The reaction solution was cooled to room temperature and 60 parts by weight of water was added to separate the solution. The obtained organic layer was washed with a 5% by weight sodium hydrogen carbonate aqueous solution and then with a 5% by weight solution of sodium chloride in water and then concentrated under reduced pressure to obtain 41.0 parts by weight of a mixture (oily) of dimethyl 2-(4-nitrophenoxy)fumarate and dimethyl 2-(4-nitrophenoxy)maleate. The combined content of dimethyl 2-(4-nitrophenoxy)fumarate and dimethyl 2-(4-nitrophenoxy)maleate was 55.8% by weight and the yield based on 2-nitrophenol was 56.9%.

Example 13

A reaction container equipped with a stirrer, a cooling tube and a thermometer was charged with 250 parts by weight of chlorosulfonic acid. Thereto, 50 parts by weight of a mixture (content: 82.1% by weight, fumaric acid/maleic acid ratio=58/42) of dimethyl 2-(2-nitrophenoxy)fumarate and dimethyl 2-(2-nitrophenoxy)maleate was added dropwise at an inner temperature of 50° C. or below. After completion of addition, the inner temperature was raised to 70° C. and the mixture was stirred and kept at the same temperature for 6 hours to obtain a reaction solution containing 8-nitro-2-methoxycarbonyl-4-oxo-4H-1-benzopyran (reaction yield: 92%). After cooled to room temperature, the reaction solution was gradually added into 300 parts by weight of water. The mixture was kept at an inner temperature of 60° C. for 1 hour and then gradually cooled to an inner temperature of 0° C. Precipitated crystals were filtered and dried to obtain 30 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 58.5% by weight; the content of 8-nitro-2-carboxy-4-oxo-4H-1-benzopyran: 39.8% by weight). The yield of 8-nitro-2-methoxycarbonyl-4-oxo-4H-1-benzopyran was 32% and the yield of 8-nitro-2-carboxy-4-oxo-4H-1-benzopyran was 50%.

Example 14

After a reaction container equipped with a stirrer, a cooling tube and a thermometer was charged with 25 parts by weight of chlorosulfonic acid, 5 parts by weight of a mixture (content: 65.7% by weight) containing 2-(2-nitrophenoxy)fumaric acid and 2-(2-nitrophenoxy)maleic acid was added. After that, the inner temperature was raised to 60° C. and the mixture was stirred and kept at the same temperature for 6 hours to obtain a reaction solution containing 8-nitro-2-carboxy-4-oxo-4H-1-benzopyran (reaction yield: 70%). After cooled to room temperature, the reaction solution was gradually added into 50 parts by weight of water and the mixture was gradually cooled to an inner temperature of 0° C. Precipitated crystals were filtered and dried to obtain 2.2 parts by weight of 8-nitro-2-carboxy-4-oxo-4H-1-benzopyran as crystals (content: 96.9% by weight, yield: 65%).

Example 15

After a reaction container equipped with a stirrer, a cooling tube and a thermometer was charged with 15 parts by weight of chlorosulfonic acid, 3 parts by weight of a mixture (content: 84.4% by weight, fumaric acid/maleic acid ratio=49/51) containing diethyl 2-(2-nitrophenoxy)fumarate and diethyl 2-(2-nitrophenoxy)maleate was added dropwise at an inner temperature of 50° C. or below. After completion of addition, the inner temperature was raised to 70° C. and the mixture was stirred and kept at the same temperature for 7 hours to obtain a reaction solution containing 8-nitro-2-ethoxycarbonyl-4-oxo-4H-1-benzopyran (reaction yield: 70%). After cooled to room temperature, the reaction solution was gradually added into 24 parts by weight of water. After kept at an inner temperature of 60° C. for 1 hour, the mixture was gradually cooled to an inner temperature of 0° C. Precipitated crystals were filtered and dried to obtain 1.3 parts by weight of a crystalline mixture containing 8-nitro-2-ethoxycarbonyl-4-oxo-4H-1-benzopyran and 8-nitro-2-carboxy-4-oxo-4H-1-benzopyran (the content of 8-nitro-2-ethoxycarbonyl-4-oxo-4H-1-benzopyran: 0.1% by weight; the content of 8-nitro-2-carboxy-4-oxo-4H-1-benzopyran: 86.4% by weight). The yield of 8-nitro-2-ethoxycarbonyl-4-oxo-4H-1-benzopyran was 0.1% and the yield of 8-nitro-2-carboxy-4-oxo-4H-1-benzopyran was 64%.

Example 16

After a reaction container equipped with a stirrer, a cooling tube and a thermometer was charged with 20 parts by weight of fuming sulfuric acid, 2 parts by weight of a mixture (content: 65.7% by weight) containing 2-(2-nitrophenoxy)fumaric acid and 2-(2-nitrophenoxy)maleic acid was added. After that, the mixture was stirred and kept at an inner temperature of 25° C. for 2 hours and then at an inner temperature of 50° C. for 2 hours to obtain a reaction solution containing 8-nitro-2-carboxy-4-oxo-4H-1-benzopyran (reaction yield: 35%). After cooled to room temperature, the reaction solution was gradually added into 40 parts by weight of water and the mixture was gradually cooled to an inner temperature of 0° C. Precipitated crystals were filtered and dried to obtain 0.28 parts by weight of 8-nitro-2-carboxy-4-oxo-4H-1-benzopyran as crystals (content: 95.2% by weight, yield: 20%).

Example 17

A reaction container equipped with a stirrer, a cooling tube and a thermometer was charged with 300 parts by weight of chlorosulfonic acid. Thereto, 60 parts by weight of a mixture (content: 81.1% by weight, fumaric acid/maleic acid ratio=57/43) containing dimethyl 2-(2-nitrophenoxy) fumarate and dimethyl 2-(2-nitrophenoxy)maleate was added dropwise at an inner temperature of 50° C. or below. After completion of addition, the inner temperature was raised to 60° C. and the mixture was stirred and kept at the same temperature for 5 hours and at an inner temperature of 70° C. for 3 hours to obtain a reaction solution containing 8-nitro-2-methoxycarbonyl-4-oxo-4H-1-benzopyran (reaction yield: 86%). After cooled to room temperature, the reaction solution was poured gradually into 360 parts by weight of water. The mixture was kept at an inner temperature of 60° C. for 8 hours and then cooled to an inner temperature of 0° C. gradually. Precipitated crystals were filtered and dried to obtain 30 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 2.5% by weight; the content of 8-nitro-2-carboxy-4-oxo-4H-1-benzopyran: 96.7% by weight). The yield of 8-nitro-2-methoxycarbonyl-4-oxo-4H-1-benzopyran was 2% and the yield of 8-nitro-2-carboxy-4-oxo-4H-1-benzopyran was 73%.

Example 18

A reaction container equipped with a stirrer, a cooling tube and a thermometer was charged with 200 parts by weight of chlorosulfonic acid. Thereto, 40 parts by weight of the mixture containing dimethyl 2-(2-nitrophenoxy)fumarate and dimethyl 2-(2-nitrophenoxy)maleate obtained in Example 4 was added dropwise at an inner temperature of 50° C. or below. After completion of addition, the inner temperature was raised to 70° C. and the mixture was stirred and reacted at the same temperature for 6 hours to obtain a reaction solution containing 8-nitro-2-methoxycarbonyl-4-oxo-4H-1-benzopyran (reaction yield based on 2-nitrophenol: 80%). After cooled to room temperature, the reaction solution was poured so gradually into 200 parts by weight of water as to keep an inner temperature of 60° C. or lower. The inner temperature was adjusted to 60° C. and the reaction mixture was kept at the same temperature for 1 hour and then gradually cooled to an inner temperature of 0° C. Precipitated crystals were filtered and dried to obtain 19.2 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 9.5% by weight; the content of 8-nitro-2-carboxy-4-oxo-4H-l-benzopyran: 85.7% by weight).

Based on 2-nitrophenol, the yield of 8-nitro-2-methoxycarbonyl-4-oxo-4H-1-benzopyran was 5.4% and the yield of 8-nitro-2-carboxy-4-oxo-4H-1-benzopyran was 51.4%.

Example 19

A reaction container equipped with a stirrer, a cooling tube and a thermometer was charged with 20 parts by weight of chlorosulfonic acid and 4 parts by weight of the mixture containing dimethyl 2-(2-nitrophenoxy)fumarate and dimethyl 2-(2-nitrophenoxy)maleate obtained in Example 9 was dropwise added thereto at an inner temperature of 50° C. or below. After completion of addition, the inner temperature was raised to 70° C. and the mixture was stirred and reacted at the same temperature for 6 hours to obtain a reaction solution containing 8-nitro-2-methoxycarbonyl-4-oxo-4H-1-benzopyran (reaction yield based on 2-nitrophenol: 72.7%). After cooled to room temperature, the reaction solution was poured into 24 parts by weight of water so gradually as to keep an inner temperature of 60° C. or lower. The inner temperature was adjusted to 60° C. and the reaction mixture was kept at the same temperature for 1 hour and then gradually cooled to an inner temperature of 0° C. Precipitated crystals were filtered and dried to obtain 2.0 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 36.9% by weight; the content of 8-nitro-2-carboxy-4-oxo-4H-1-benzopyran: 61.2% by weight).

Based on 2-nitrophenol, the yield of 8-nitro-2-methoxycarbonyl-4-oxo-4H-1-benzopyran was 19.3% and the yield of 8-nitro-2-carboxy-4-oxo-4H-1-benzopyran was 34.0%.

Example 20

A reaction container equipped with a stirrer, a cooling tube and a thermometer was charged with 50.2 parts by weight of chlorosulfonic acid. Thereto, 25.1 parts by weight of 98% sulfuric acid was added dropwise over 1 hour and the mixture was then warmed to 60° C. Thereto, 25.6 parts by weight of a mixture (content: 89.6% by weight, fumaric acid/maleic acid ratio=54/46) containing dimethyl 2-(2-nitrophenoxy)fumarate and dimethyl 2-(2-nitrophenoxy) maleate was added dropwise at an inner temperature of 60° C. over 6 hours. After completion of addition, the inner temperature was raised to 95° C. and the mixture was stirred and kept at the same temperature for 4 hours to obtain a reaction solution containing 8-nitro-2-methoxycarbonyl-4-oxo-4H-1-benzopyran (reaction yield: 88%). The reaction solution was poured gradually into 113 parts by weight of water at 85° C. or below. The mixture was kept at an inner temperature of 85° C. for 6 hours and then cooled gradually to an inner temperature of 25° C. Precipitated crystals were filtered and dried to obtain 16.7 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 3.8% by weight; the content of 8-nitro-2-carboxy-4-oxo-4H-1-benzopyran: 96.0% by weight). The yield of 8-nitro-2-methoxycarbonyl-4-oxo-4H-1-benzopyran was 5.3% and the yield of 8-nitro-2-carboxy-4-oxo-4H-1-benzopyran was 81.5%.

Example 21

A reaction container equipped with a stirrer, a cooling tube and a thermometer was charged with 50.2 parts by weight of chlorosulfonic acid. Thereto, 25.0 parts by weight of 98% sulfuric acid was added dropwise over 1 hour and the mixture was then warmed to 60° C. Thereto, 25.3 parts by weight of the mixture (content: 89.6% by weight, fumaric acid/maleic acid ratio=54/46) containing dimethyl 2-(2-nitrophenoxy)fumarate and dimethyl 2-(2-nitrophenoxy) maleate obtained in Example 10 was added dropwise at an inner temperature of 60° C. over 4 hours. After completion of addition, the inner temperature was raised to 95° C. and the mixture was stirred and kept at the same temperature for 4 hours to obtain a reaction solution containing 8-nitro-2-methoxycarbonyl-4-oxo-4H-1-benzopyran (reaction yield: 88%). The reaction solution was poured gradually into 113 parts by weight of water at 85° C. or below. The mixture was kept at an inner temperature of 85° C. for 6 hours and then cooled gradually to an inner temperature of 25° C. Precipitated crystals were filtered and dried to obtain 16.3 parts by weight of a crystalline mixture of 8-nitro-2-methoxycarbonyl-4-oxo-4H-1-benzopyran and 8-nitro-2-carboxy-4-oxo-4H-1-benzopyran (the content of 8-nitro-2-methoxycarbonyl-4-oxo-4H-1-benzopyran: 13.8% by weight; the content of 8-nitro-2-carboxy-4-oxo-4H-1-benzopyran: 84.6% by weight). The yield of 8-nitro-2-methoxycarbonyl-4-oxo-4H-1-benzopyran was 11.5% and the yield of 8-nitro-2-carboxy-4-oxo-4H-1-benzopyran was 74.0%.

Example 22

A reaction container equipped with a stirrer, a cooling tube and a thermometer was charged with 79.3 parts by weight of chlorosulfonic acid and warmed to 60° C. Thereto 20.2 parts by weight of a mixture (content: 55.8% by weight, isomer ratio=52/48) containing dimethyl 2-(4-nitrophenoxy) fumarate and dimethyl 2-(4-nitrophenoxy)maleate was added at an inner temperature of 60° C. The inner temperature was raised to 100° C. and the mixture was stirred and kept at the same temperature for 6 hours to obtain a reaction solution containing 6-nitro-2-methoxycarbonyl-4-oxo-4H-1-benzopyran (reaction yield: 95%). The reaction solution was poured gradually into 120 parts by weight of water at 60° C. and the mixture was kept at an inner temperature of 60° C. for 1 hour and then cooled gradually to an inner temperature of 25° C. Precipitated crystals were filtered and dried to obtain 10.8 parts by weight of a crystalline mixture of 6-nitro-2-methoxycarbonyl-4-oxo-4H-1-benzopyran and 6-nitro-2-carboxy-4-oxo-4H-1-benzopyran (the content of 6-nitro-2-methoxycarbonyl-4-oxo-4H-1-benzopyran: 23.0% by weight; the content of 6-nitro-2-carboxy-4-oxo-4H-1-benzopyran: 58.5% by weight). The yield of 6-nitro-2-methoxycarbonyl-4-oxo-4H-1-benzopyran was 24.9% and the yield of 6-nitro-2-carboxy-4-oxo-4H-1-benzopyran was 58.5%.

Example 23

A reaction container equipped with a stirrer, a cooling tube and a thermometer was charged with 90 parts by weight of a nitrochromonecarboxylic acid mixture (a mixture of 8-nitro-2-carboxy-4-oxo-4H-1-benzopyran (content: 47.1%) and 8-nitro-2-methoxycarbonyl-4-oxo-4H-1-benzopyran (content: 51.6%)), 540 parts by weight of methanol and 9.78 parts by weight of 96% sulfuric acid and the mixture was heated to the reflux temperature and then refluxed for 11 hours under heating. The reaction solution was then cooled to room temperature to obtain 633 parts by weight of a methanol solution containing a crystal of 8-nitro-2-methoxycarbonyl-4-oxo-4H-1-benzopyran. The yield of 8-nitro-2-methoxycarbonyl-4-oxo-4H-1-benzopyran was 98%.

Example 24

A reaction container equipped with a stirrer, a cooling tube and a thermometer was charged with 9.97 parts by weight of a nitrochromonecarboxylic acid mixture (a mixture of 8-nitro-2-carboxy-4-oxo-4H-1-benzopyran (content: 96%) and 6-nitro-2-methoxycarbonyl-4-oxo-4H-1-benzopyran (content: 3.7%)), 29.9 parts by weight of toluene and 0.09 parts by weight of dimethylformamide and the mixture was warmed to 50° C. After 5.09 parts by weight of thionyl chloride was added dropwise over 0.5 hours, the mixture was kept warm for 9.5 hours. Another 1.0 parts by weight of thionyl chloride was added thereto and the mixture was kept warm for 2 hours. After cooled to room temperature, the mixture was concentrated to half volume to remove excess thionyl chloride. The residue was cooled to 10° C. and 2.99 parts by weight of ethanol was added dropwise thereto over 0.5 hour at an inner temperature of 15° C. or below. After completion of addition, the obtained mixture was warmed to room temperature. After 19.94 parts by weight of water was added, precipitates were filtered off with Celite and washed thoroughly with 10 parts by weight of toluene. After the filtrate was allowed to stand still to separate an aqueous layer, a toluene layer was mixed with 10 parts by weight of water and adjusted to pH 4.5 with a 10% sodium carbonate aqueous solution. After an aqueous layer was separated, a toluene layer was concentrated and dried to obtain 10.63 parts by weight of a nitrochromone ester mixture (a mixture of 8-nitro-2-ethoxycarbonyl-4-oxo-4H-1-benzopyran (content: 94.5%) and 8-nitro-2-methoxycarboxy-4-oxo-4H-1-benzopyran (content: 3.5%)) as a pale yellow solid. The yield of 8-nitro-2-ethoxycarbonyl-4-oxo-4H-1-benzopyran was 94%.

Example 25

A reaction container equipped with a stirrer, a cooling tube and a thermometer was charged with 8 parts by weight of a nitrochromonecarboxylic acid mixture (a mixture of 8-nitro-2-carboxy-4-oxo-4H-1-benzopyran (content: 96.8%) and 8-nitro-2-methoxycarbonyl-4-oxo-4H-1-benzopyran (content: 3.1%)), 24 parts by weight of ethyl acetate and then 3.7 parts by weight of triethylamine, and warmed to 70° C. Thereto 5.5 parts by weight of diethyl sulfate was added dropwise over 1 hour and the resulting mixture was kept at 70° C. for 5 hours. Thereto 54.8 parts by weight of ethyl acetate and 12 parts by weight of water were added and the mixture was cooled to room temperature. An aqueous layer was separated and an ethyl acetate layer was washed with 9.7 parts by weight of 5% sulfuric acid and 8 parts by weight of water to obtain 84.74 parts by weight of a solution of nitrochromone ester mixture in ethyl acetate (a mixture of 8-nitro-2-ethoxycarbonyl-4-oxo-4H-1-benzopyran (content: 9.9%) and 8-nitro-2-methoxycarbonyl-4-oxo-4H-1-benzopyran (content: 0.3%)). The yield of 8-nitro-2-ethoxycarbonyl-4-oxo-4H-1-benzopyran was 98%.

Example 26

A reaction container equipped with a stirrer, a cooling tube and a thermometer was charged with 240 parts by weight of nitrochromonecarboxylic acid mixture (a mixture of 8-nitro-2-carboxy-4-oxo-4H-1-benzopyran (content:

95.9%) and 8-nitro-2-methoxycarbonyl-4-oxo-4H-1-benzopyran (content: 3.7%)) and 955 parts by weight of ethyl acetate, and 19.4 parts by weight of water and 125 parts by weight of triethylamine were further added. After the mixture was warmed to 70° C., 186.6 parts by weight of diethyl sulfate was added dropwise over 3 hours and the resulting mixture was kept at 70° C. for 6 hours. Thereto 238 parts by weight of ethyl acetate and 152.8 parts by weight of a 15% solution of sodium chloride in water were added and the mixture was cooled to 50° C. to separate an aqueous layer. Then, 179 parts by weight of water and 7.3 parts by weight of 10% sulfuric acid were added and an aqueous layer was separated to obtain 1,421.8 parts by weight of a solution of a nitrochromone ester mixture in ethyl acetate (a mixture of 8-nitro-2-ethoxycarbonyl-4-oxo-4H-1-benzopyran (content: 17.8%) and 8-nitro-2-methoxycarbonyl-4-oxo-4H-1-benzopyran (content: 0.5%)). The yield of 8-nitro-2-ethoxycarbonyl-4-oxo-4H-1-benzopyran was 98%.

Example 27

A reaction container equipped with a stirrer, a cooling tube and a thermometer was charged with 10 parts by weight of ethanol, 1 part by weight of 8-nitro-2-ethoxycarbonyl-4-oxo-4H-1-benzopyran (content: 96.4% by weight), 0.2 part by weight of 5% by weight palladium/carbon (water content: 50% by weight) and 0.17 parts by weight of pyridine at room temperature, and purged with nitrogen and then hydrogen under the normal pressure. The container was kept at inner temperature of 15 to 25° C. and supplied with hydrogen for 5 hours under the normal pressure. After that, the container was purged with nitrogen to stop the reaction. The reaction solution was filtered to remove insoluble substances such as palladium/carbon and obtain a solution containing 8-amino-2-ethoxycarbonyl-4-oxo-4H-1-benzopyran.

The filtered insoluble substances were washed with acetonitrile and the washing solution was mixed with the previously obtained filtrate. The mixture was concentrated under reduced pressure to obtain 0.85 part by weight of 8-amino-2-ethoxycarbonyl-4-oxo-4H-1-benzopyran as yellow crystals. The crystals were subjected to LC analysis (absolute calibration method) to find that the content was 91% by weight and the yield was 89%. It was also found that the yields of over-reduced compounds in the crystals: 8-amino-2-ethoxycarbonyl-4-hydroxy-3,4-dihydro-2H-1-benzopyran (hereinafter, referred as the over-reduced compound A), 8-amino-2-ethoxycarbonyl-3,4-dihydro-2H-1-benzopyran (hereinafter, referred as the over-reduced compound B) and 8-amino-2-ethoxycarbonyl-4-oxochromane (hereinafter, referred as the over-reduced compound C) were 0.5%, below the detection limit and 8.2% respectively.

Example 28

A reaction container equipped with a stirrer, a cooling tube and a thermometer was charged with 30 parts by weight of ethyl acetate, 4 parts by weight of 8-nitro-2-ethoxycarbonyl-4-oxo-4H-1-benzopyran (content: 95.4% by weight), 0.77 part by weight of sodium carbonate and 0.38 part by weight of 5% by weight palladium/carbon (water content: 50% by weight) at room temperature, and purged with nitrogen and then hydrogen under the normal pressure. The container was kept at an inner temperature of 28 to 32° C. and supplied with hydrogen for 4 hours under the normal pressure. After that, the container was purged with nitrogen to stop the reaction. After 30 parts by weight of tetrahydrofuran was added and the reaction solution was kept warm for 30 minutes, the solution was filtered to remove insoluble substances such as palladium/carbon and obtain a solution containing 8-amino-2-ethoxycarbonyl-4-oxo-4H-1-benzopyran. The solution was analyzed by LC analysis to find that the yield of 8-amino-2-ethoxycarbonyl-4-oxo-4H-1-benzopyran was 92%. The yields of the over-reduced compounds A and B were below the detection limit and the yield of the over-reduced compound C was 4.8%.

Example 29

A reaction container equipped with a stirrer, a cooling tube and a thermometer was charged with 30 parts by weight of ethyl acetate, 4 parts by weight of 8-nitro-2-ethoxycarbonyl-4-oxo-4H-1-benzopyran (content: 95.4% by weight), 0.61 part by weight of sodium hydrogen carbonate and 0.38 part by weight of 5% by weight palladium/carbon (water content: 50% by weight) at room temperature, and purged with nitrogen and then hydrogen under the normal pressure. The container was kept at an inner temperature of 28 to 32° C. and supplied with hydrogen for 4 hours under the normal pressure. After that, the container was purged with nitrogen to stop the reaction. After 30 parts by weight of tetrahydrofuran was added and the reaction solution was kept warm for 30 minutes, the solution was filtered to remove insoluble substances such as palladium/carbon and obtain a solution containing 8-amino-2-ethoxycarbonyl-4-oxo-4H-1-benzopyran. The solution was analyzed by LC analysis to find that the yield of 8-amino-2-ethoxycarbonyl-4-oxo-4H-1-benzopyran was 94%. The yields of the over-reduced compounds A and B were below the detection limit and the yield of the over-reduced compound C was 5.2%.

Example 30

A reaction container equipped with a stirrer, a cooling tube and a thermometer was charged with 30.5 parts by weight of ethyl acetate, 4 parts by weight of 8-nitro-2-ethoxycarbonyl-4-oxo-4H-1-benzopyran (content: 95.4% by weight), 0.59 part by weight of sodium acetate and 0.38 part by weight of 5% by weight palladium/carbon (water content: 50% by weight) at room temperature, and purged with nitrogen and then hydrogen under the normal pressure. The container was kept at an inner temperature of 28 to 32° C. and supplied with hydrogen for 5 hours under the normal pressure. After that, the container was purged with nitrogen to stop the reaction. After 30 parts by weight of tetrahydrofuran was added and the reaction solution was kept warm for 30 minutes, the solution was filtered to remove insoluble substances such as palladium/carbon and obtain a solution containing 8-amino-2-ethoxycarbonyl-4-oxo-4H-1-benzopyran. The solution was analyzed by LC analysis to find that the yield of 8-amino-2-ethoxycarbonyl-4-oxo-4H-1-benzopyran was 97%. The yields of the over-reduced compounds A and B were below the detection limit and the yield of the over-reduced compound C was 2.9%.

Example 31

A reaction container equipped with a stirrer, a cooling tube and a thermometer was charged with 20 parts by weight of a solution (content: 18.0% by weight) of 8-nitro-2-ethoxycarbonyl-4-oxo-4H-1-benzopyran in ethyl acetate, 13.4 parts by weight of ethyl acetate, a mixture of 0.19 part by weight of 5% by weight palladium/carbon (water content: 50% by weight) and 0.56 part by weight of sodium acetate, and 1.1 parts by weight of water at room temperature, and purged with nitrogen and then hydrogen under the normal pressure. The container was kept at an inner temperature of 38 to 42° C. and supplied with hydrogen for 4 hours under the normal pressure. After that, the container was purged with nitrogen to stop the reaction. After 33 parts by weight of acetonitrile was added and the reaction solution was kept warm for 30 minutes, the solution was filtered to remove insoluble substances such as palladium/carbon and obtain a solution containing 8-amino-2-ethoxycarbonyl-4-oxo-4H-1-benzopyran. The solution was analyzed by LC analysis to find that the yield of 8-amino-2-ethoxycarbonyl-4-oxo-4H-1-benzopyran was 94%. The yields of the over-reduced compounds A and B were below the detection limit and the yield of the over-reduced compound C was 1.8%.

Example 32

A pressurized reaction container made of glass and equipped with a stirrer and a thermometer was charged with 507 parts by weight of a solution (content: 17.7% by weight) of 8-nitro-2-ethoxycarbonyl-4-oxo-4H-1-benzopyran in ethyl acetate, 122 parts by weight of ethyl acetate, 1.4 parts by weight of sodium acetate, 1.8 parts by weight of 5% by weight palladium/carbon (water content: 50% by weight) and 14.4 parts by weight of water which were mixed previously, and purged with nitrogen under 0.4 MPa 5 times and then hydrogen under 0.66 MPa 5 times. While the hydrogen pressure was kept at 0.66 MPa and the inner temperature was kept at 50 to 56° C., the container was supplied with hydrogen for 9 hours. After that, the container was purged with nitrogen to stop the reaction. The reaction solution was heated to 70° C. and then hot filtered to remove insoluble substances such as palladium/carbon. After an aqueous layer was separated, a solution containing 8-amino-2-ethoxycarbonyl-4-oxo-4H-1-benzopyran was obtained. The solution was analyzed by LC analysis to find that the yield of 8-amino-2-ethoxycarbonyl-4-oxo-4H-1-benzopyran was 93%. The yields of the over-reduced compounds A and B were below the detection limit and the yield of the over-reduced compound C was 4%.

The solution thus obtained was loaded into a reaction container equipped with a stirrer, a cooling tube and a thermometer and the inner temperature was adjusted to 60° C. Under a reduced pressure of 60 kPa, 153 parts by weight of ethyl acetate was distilled off. The pressure in the container was turned back to the normal pressure and a seed crystal of 8-amino-2-ethoxycarbonyl-4-oxo-4H-1-benzopyran was added to the solution at an inner temperature of 58° C. After the solution was cooled to 40° C. in 2 hours, 260 parts by weight of ethyl acetate was distilled off under a reduced pressure of 26.6 kPa. The pressure was turned back to the normal pressure and the solution was cooled to 0° C. in 4 hours, kept for 1 hour, filtered and then dried to obtain 66.5 parts by weight of 8-amino-2-ethoxycarbonyl-4-oxo-4H-1-benzopyran. The obtained crystals were analyzed by LC analysis to find that the purity was about 100% by weight and the yield was 94% (total yield: 88%).

Comparative Example 2

A reaction container equipped with a stirrer, a cooling tube and a thermometer was charged with 10 parts by weight of ethanol, 1 part by weight of 8-nitro-2-ethoxycarbonyl-4-oxo-4H-1-benzopyran (content: 96.4% by weight) and 0.2 part by weight of 5% by weight palladium/carbon (water content: 50% by weight) at room temperature, and purged with nitrogen and then hydrogen under the normal pressure. The container was kept at an inner temperature of 15 to 25° C. and supplied with hydrogen for 5 hours under the normal pressure. The container was further supplied with hydrogen at an inner temperature of 40° C. for 3 hours and then purged with nitrogen to stop the reaction. The reaction solution was filtered to remove insoluble substances such as palladium/carbon and obtain a solution containing 8-amino-2-ethoxycarbonyl-4-oxo-4H-1-benzopyran.

The filtered insoluble substances were washed with acetonitrile and the washing solution was mixed with the previously obtained filtrate. The mixture was concentrated under reduced pressure to obtain 0.85 part by weight of 8-amino-2-ethoxycarbonyl-4-oxo-4H-1-benzopyran as golden yellow and sticky crystals. The crystals were subjected to LC analysis (absolute calibration method) to find that the content was 67% by weight and the yield was 64%. It was also found that the yields of the over-reduced compounds A, B and C in the crystals were 12.2%, 0.1% (LC area percentage value) and 17.7% respectively.

Comparative Example 3

A reaction container equipped with a stirrer, a cooling tube and a thermometer was charged with 10 parts by weight of ethanol, 1 part by weight of 8-nitro-2-ethoxycarbonyl-4-oxo-4H-1-benzopyran (content: 96.4% by weight), 0.13 part by weight of acetic acid and 0.2 part by weight of 5% by weight palladium/carbon (water content: 50% by weight) at room temperature, and purged with nitrogen and then hydrogen under the normal pressure. The container was kept at an inner temperature of 15 to 25° C. and supplied with hydrogen for 4 hours under the normal pressure. The container was further supplied with hydrogen at an inner temperature of 40° C. for 2 hours and then purged with nitrogen to stop the reaction. The reaction solution was filtered to remove insoluble substances such as palladium/carbon and obtain a solution containing 8-amino-2-ethoxycarbonyl-4-oxo-4H-1-benzopyran.

The filtered insoluble substances were washed with acetonitrile and the washing solution was mixed with the previously obtained filtrate. The mixture was concentrated under reduced pressure to obtain 0.9 part by weight of 8-amino-2-ethoxycarbonyl-4-oxo-4H-1-benzopyran as brown and sticky crystals. The crystals were subjected to LC analysis (absolute calibration method) to find that the content was 60% by weight and the yield was 62%. It was also found that the yields of the over-reduced compounds A, B and C in the crystals were 5.5%, 1% (LC area percentage value) and 11.5% respectively.

Comparative Example 4

A reaction container equipped with a stirrer, a cooling tube and a thermometer was charged with 25 parts by weight of a solution (content: 18.0% by weight) of 8-nitro-2-ethoxycarbonyl-4-oxo-4H-1-benzopyran in ethyl acetate, 7.5 parts by weight of ethyl acetate and a mixture of 0.09 part by weight of 5% by weight palladium/carbon (water content: 50% by weight) and 0.4 part by weight of water, and purged with nitrogen and then hydrogen under the normal pressure. The container was kept at an inner temperature of 55° C. and supplied with hydrogen for 4.5 hours under the normal pressure. After that, the container was purged with nitrogen to stop the reaction. Then, 32 parts by weight of ethyl acetate was added and the reaction solution was kept warm for 30 minutes and filtered to remove insoluble substances such as palladium/carbon and obtain a solution containing 8-amino-2-ethoxycarbonyl-4-oxo-4H-1-benzopyran. The solution was subjected to LC analysis to find that the yield of 8-amino-2-ethoxycarbonyl-4-oxo-4H-1-benzopyran was 82%. It was found that the yields of the over-reduced compounds A, B and C in the solution were 0.9%, below the detection limit and 13.9% respectively.

Example 33

A reaction container equipped with a stirrer, a cooling tube and a thermometer was charged with 100 parts by weight of crystals of 8-nitro-2-carboxy-4-oxo-4H-1-benzopyran (content: 96.0% by weight, containing 3.8% by weight of 8-nitro-2-methoxycarbonyl-4-oxo-4H-1-benzopyran) obtained in Example 20 and 427.9 parts by weight of ethyl acetate, and 25.0 parts by weight of water and 41.69 parts by weight of triethylamine were further added, warmed to an inner temperature of 60° C. and kept at the same temperature for 6 hours. Thereafter, the pressure in the container was reduced to 40 kPa, and the reaction mixture was refluxed and dehydrated under reduced pressure for 7 hours. After the pressure was turned back, 82.1 parts by weight of volatile ethyl acetate and 2.1 parts by weight of triethylamine were added into the container and the mixture was heated to 70° C. Then, 64.8 parts by weight of diethyl sulfate was added dropwise over 3 hours and the mixture was kept at the same temperature for 4 hours. Further, 3.9 parts by weight of triethylamine and 6.1 parts by weight of diethyl sulfate were added and the mixture was kept warm for 3 hours. After 100 parts by weight of ethyl acetate and 64 parts by weight of 15% by weight solution of sodium chloride in water were added, the mixture was cooled to an inner temperature of 50° C. and then separated. To the obtained organic layer, 75 parts by weight of water and 2.4 parts by weight of 10% by weight sulfuric acid were added and the solution was separated to obtain 574.5 parts by weight of an organic layer containing 8-nitro-2-ethoxycarbonyl-4-oxo-4H-1-benzopyran (content: 18.0% by weight). The yield: 96%. The organic layer contained 8-nitro-2-methoxycarbonyl-4-oxo-4H-1-benzopyran in an amount of 0.5% by weight.

A reaction container equipped with a stirrer and a thermometer was charged with 561.7 parts by weight of the above obtained solution of 8-nitro-2-ethoxycarbonyl-4-oxo-4H-1-benzopyran in ethyl acetate(content: 18.0% by weight, containing 0.5% by weight of 8-nitro-2-methoxycarbonyl-4-oxo-4H-1-benzopyran), 167.7 parts by weight of ethyl acetate, 1.6 parts by weight of sodium acetate, 1.6 parts by weight of 5% by weight palladium/carbon (water content: 50% by weight) and 6.3 parts by weight of water. The container was purged with nitrogen and then with hydrogen under the normal pressure. The container was kept at an inner temperature of 50 to 57° C. and supplied with hydrogen for 4 hours under the normal pressure. After that, the container was additionally charged with 0.5 part by weight of 5% by weight palladium/carbon (water content: 50% by weight) and 2.1 parts by weight of water and further supplied with hydrogen for 15 hours. After that, the container was purged with nitrogen to stop the reaction. After the inner temperature was raised to 70° C., the reaction solution was filtered at the same temperature and substances adhered to the container were thoroughly washed with 104 parts by weight of ethyl acetate to remove insoluble substances such as palladium/carbon. The filtrate was allowed to stand still and an aqueous layer was removed to obtain an organic layer containing 800 parts by weight of 8-amino-2-ethoxycarbonyl-4-oxo-4H-1-benzopyran (content: 10.8% by weight). The yield: 95%. The organic layer contained 8-amino-2-methoxycarbonyl-4-oxo-4H-1-benzopyran in an amount of 0.3% by weight. The yields of the over-reduced compounds A and B were below the detection limit and the over-reduced compound C was produced in 2% yield.

A reaction container equipped with a stirrer, a cooling tube and a thermometer was charged with 765 parts by weight of the above obtained solution of 8-amino-2-ethoxycarbonyl-4-oxo-4H-1-benzopyran in ethyl acetate (content: 10.8% by weight, containing 0.3% by weight of 8-amino-2-methoxycarbonyl-4-oxo-4H-1-benzopyran) and adjusted to an inner temperature of 48° C. After a seed crystal was added, the solution was gradually cooled to an inner temperature of 40° C. and concentrated under a reduced pressure of 26.6 kPa to remove 492 parts by weight of ethyl acetate. The pressure in the container was turned back again to the normal pressure and the inner temperature was decreased to 0° C. The reaction solution was kept at 0° C. for 1 hour and then filtered to obtain precipitated crystals, which were dried to obtain 82.2 parts by weight of 8-amino-2-ethoxycarbonyl-4-oxo-4H-1-benzopyran as crystals (the yield of the crystals: 95%). The yield based on 8-nitro-2-ethoxycarbonyl-4-oxo-4H-1-benzopyran: 90%. The crystals contained 8-amino-2-methoxycarbonyl-4-oxo-4H-1-benzopyran in an amount of 1.7% by weight.

A reaction container equipped with a stirrer, a cooling tube and a thermometer was charged with 45 parts by weight of the above obtained 8-amino-2-ethoxycarbonyl-4-oxo-4H-1-benzopyran (containing 1.7% by weight of 8-amino-2-methoxycarbonyl-4-oxo-4H-1-benzopyran), 29 parts by weight of 5-ethyl-2-methylpyridine and 495 parts by weight of toluene. The inner temperature was increased to 60° C. and at the same temperature, 286.8 parts by weight of a solution (content: 20.4% by weight) of 4-(4-phenylbutoxy) benzoic acid chloride in toluene was added dropwise over 3 hours. After the resulting solution was further stirred and kept for 5 hours at the same temperature, a 20% by weight sulfuric acid aqueous solution was added and the resulting mixture was warmed to an inner temperature of 80° C. and then separated. The obtained organic layer was washed with a 20% by weight sulfuric acid aqueous solution and then with water and gradually cooled to 50° C. The organic layer was concentrated under reduced pressure to remove 260 parts by weight of toluene and then cooled gradually to an inner temperature of 0° C. to precipitate crystals, which were filtrated. The obtained crystals were washed and dried to obtain 90.7 parts by weight of 8-[4-(4-phenylbutoxy)benzoyl]amino-2-ethoxycarbonyl-4-oxo-4H-1-benzopyran (containing 1.8% by weight of 8-[4-(4-phenylbutoxy)benzoyl]amino-2-methoxycarbonyl-4-oxo-4H-1-benzopyran). The yield based on 8-amino-2-ethoxycarbonyl-4-oxo-4H-1-benzopyran: 97%.

A reaction container equipped with a stirrer, a cooling tube and a thermometer was charged with 45 parts by weight of the above obtained 8-[4-(4-phenylbutoxy)benzoyl]

amino-2-ethoxycarbonyl-4-oxo-4H-1-benzopyran (containing 1.8% by weight of 8-[4-(4-phenylbutoxy)benzoyl]amino-2-methoxycarbonyl-4-oxo-4H-1-benzopyran) and 180 parts by weight of monochlorobenzene. At an inner temperature of 25° C., 58.8 parts by weight of a solution of ammonia in methanol (content: 16.1% by weight) was added dropwise over 2 hours and the reaction solution was further stirred and kept at the same temperature for 6 hours. The obtained reaction mass was warmed to an inner temperature of 60° C. to remove excess ammonia gas. Then, in order to remove methanol, the reaction mass was further warmed to 80° C. and kept at the same temperature for 30 minutes. Next, the reaction mass was cooled to 50° C. and concentrated under a reduced pressure of 13.3 kPa so that residual methanol was 0.1% or less. To the concentrated mass, 6.8 parts by weight of 5-ethyl-2-methylpyridine and 4.4 parts by weight of methanesulfonic acid were added and the mixture was heated to 100° C., stirred and kept at the same temperature for 4 hours. After the reaction mass was cooled to 65° C., 45 parts by weight of methanol was added dropwise thereto and the mixture was cooled gradually to 0° C. to precipitate crystals. The crystals were filtered, washed and then dried to obtain 41 parts by weight of 8-[4-(4-phenylbutoxy)benzoyl]amino-2-carbamoyl-4-oxo-4H-1-benzopyran. The yield based on 8-[4-(4-phenylbutoxy)benzoyl]amino-2-ethoxycarbonyl-4-oxo-4H-1-benzopyran: 96%.

A reaction container equipped with a stirrer, a cooling tube and a thermometer was charged with 288 parts by weight of 5-ethyl-2-methylpyridine and 43.7 parts by weight of phosphorus oxychloride and the inner temperature was increased to 60° C. The mixture was stirred and kept at the same temperature for 2 hours. After cooled to 40° C., 72 parts by weight of 8-[4-(4-phenylbutoxy)benzoyl]amino-2-carbamoyl-4-oxo-4H-1-benzopyran obtained as described above and 360 parts by weight of toluene were charged and the mixture was stirred and kept at the same temperature for 6 hours. The obtained reaction mass was added to and mixed with a suspension of 634 parts by weight of toluene and 192 parts by weight of a 50% sulfuric acid aqueous solution. The mixture was then heated to 84° C., allowed to stand still and then separated. At the same temperature, the obtained organic layer was washed successively with brine twice and an aqueous sodium dihydrogenphosphate, and an activated clay and activated carbon were added thereto. After stirred for 30 minutes, the activated clay and activated carbon were removed by filtration to obtain a solution of 8-[4-(4-phenylbutoxy)benzoyl]amino-2-cyano-4-oxo-4H-benzopyran in toluene.

A flask equipped with a stirrer and a thermometer and connected to a distillation apparatus was charged with 1,236 parts by weight of water, 1.8 parts by weight of sodium dihydrogenphosphate and 0.2 part by weight of disodium hydrogenphosphate, and heated to and kept at 99° C. While the above obtained solution of 8-[4-(4-phenylbutoxy)benzoyl]amino-2-cyano-4-oxo-4H-benzopyran in toluene was poured into the separable flask at 95° C. over about 2.5 hours, toluene-water azeotrope was distilled off under the normal pressure. Soon after completion of the pouring, the distillation of toluene was completed and crystals were precipitated in the solution. The precipitated crystals were filtered, washed and dried to obtain 64 parts by weight of 8-[4-(4-phenylbutoxy)benzoyl]amino-2-cyano-4-oxo-4H-1-benzopyran. The yield based on 8-[4-(4-phenylbutoxy)benzoyl]amino-2-carbamoyl-4-oxo-4H-1-benzopyran: 92%.

Industrial Applicability

According to the present invention, an aminochromone compound useful as a pharmaceutical intermediate can be produced industrially advantageously from a dicarboxylic acid compound which can be easily derived from an easily available nitrophenol.

The invention claimed is:

1. A process for producing an aminochromone compound represented by the formula (6):

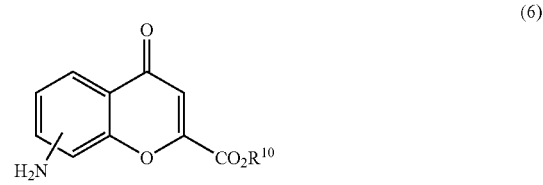

(6)

wherein $R^{10}$ is as defined below; which comprises reacting a nitrochromone compound represented by the formula (5):

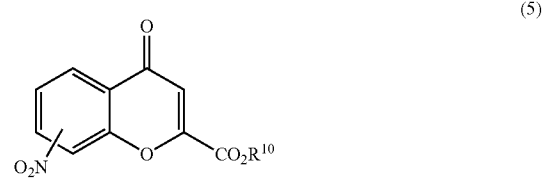

(5)

wherein $R^{10}$ represents a hydrogen atom or a lower alkyl group, with hydrogen in the presence of a metal catalyst and a base in an organic solvent.

2. The process according to claim 1, wherein the base is at least one base selected from alkali metal carbonates, alkali metal hydrogen carbonates, carboxylic acid alkali metal salts, aliphatic tertiary amines and pyridine compounds.

3. The process according to claim 1, wherein the base is at least one base selected from alkali metal hydrogen carbonates and carboxylic acid alkali metal salts.

4. The process according to claim 1, wherein $R^{10}$ is a lower alkyl group.

5. The process according to claim 4, which further comprises a step of reacting the aminochromone compound represented by the formula (6) with a reactive derivative of carboxylic acid represented by the formula (7):

$$R^{11}COZ \qquad (7)$$

wherein $R^{11}$ represents a substituted or unsubstituted aliphatic group or a substituted or unsubstituted aromatic group and Z represents a leaving group, to produce an amidochromone compound represented by the formula (8):

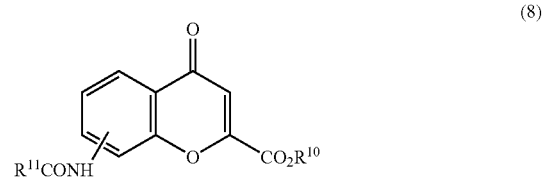

(8)

wherein $R^{10}$ and $R^{11}$ are as defined in the formulas (6) and (7).

6. The process according to claim 5, which further comprises steps of reacting the amidochromone compound represented by the formula (8) with ammonia to produce a compound represented by the formula (9):

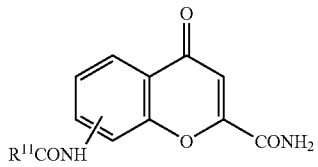

(9)

wherein $R^{11}$ is as defined in the formula (8), and then reacting the compound of the formula (9) with a dehydrating agent to produce an amidochromonenitrile compound represented by the formula (10):

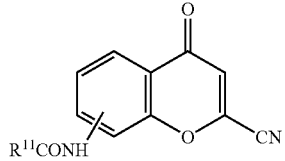

(10)

wherein $R^{11}$ is as defined above.

* * * * *